(12) United States Patent
Doron et al.

(10) Patent No.: US 8,340,776 B2
(45) Date of Patent: Dec. 25, 2012

(54) BIASED ACOUSTIC SWITCH FOR IMPLANTABLE MEDICAL DEVICE

(75) Inventors: Eyal Doron, Kiriat-Yam (IL); Lance E. Juffer, Lino Lakes, MN (US); Keith R. Maile, New Brighton, MN (US); Andrew L. Cable, Hudson, WI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 349 days.

(21) Appl. No.: 12/054,864

(22) Filed: Mar. 25, 2008

(65) Prior Publication Data
US 2008/0243210 A1  Oct. 2, 2008

Related U.S. Application Data

(60) Provisional application No. 60/908,171, filed on Mar. 26, 2007.

(51) Int. Cl.
*A61N 1/00* (2006.01)
*A61B 5/02* (2006.01)
(52) U.S. Cl. ............... 607/60; 607/62; 600/485
(58) Field of Classification Search ............ 607/60, 607/62; 600/485
See application file for complete search history.

(56) References Cited

U.S. PATENT DOCUMENTS

| | | |
|---|---|---|
| 2,786,899 A | 3/1957 | Carlisle et al. |
| 3,536,836 A | 10/1970 | Pfeiffer |
| 3,672,352 A | 6/1972 | Summers |
| 3,757,770 A | 9/1973 | Brayshaw et al. |
| 3,805,796 A | 4/1974 | Terry, Jr. et al. |
| 3,853,117 A | 12/1974 | Murr |
| 3,943,915 A | 3/1976 | Severson |
| 3,970,987 A | 7/1976 | Kolm |
| 4,026,276 A | 5/1977 | Chubbuck |
| 4,041,954 A | 8/1977 | Ohara |
| 4,062,354 A | 12/1977 | Taylor et al. |
| 4,082,097 A | 4/1978 | Mann et al. |
| 4,099,530 A | 7/1978 | Chen et al. |
| 4,127,110 A | 11/1978 | Bullara |
| 4,170,742 A | 10/1979 | Itagaki et al. |
| 4,206,761 A | 6/1980 | Cosman |
| 4,206,762 A | 6/1980 | Cosman |

(Continued)

FOREIGN PATENT DOCUMENTS
EP   0 499 939   8/1992
(Continued)

OTHER PUBLICATIONS

Harrison et al., "A Low-Power Low-Noise CMOS Amplifier for Neural Recording Applications," IEEE Journal of Solid-State Circuits 38(6):958-965, Jun. 2003.

(Continued)

*Primary Examiner* — Nicole F Lavert
(74) *Attorney, Agent, or Firm* — Faegre Baker Daniels LLP

(57) ABSTRACT

Devices, systems, and methods for selectively activating medical devices are disclosed. A medical device in accordance with an illustrative embodiment includes an energy storage device, an acoustic transducer configured to convert an acoustic signal into an electrical signal, a signal detector configured to generate a trigger signal when the electrical signal exceeds a specific threshold established by a biasing element, a control circuit, and an activation/deactivation switch configured to switch the medical device between an inactive state and an active state in response to the trigger signal.

24 Claims, 15 Drawing Sheets

U.S. PATENT DOCUMENTS

| | | | |
|---|---|---|---|
| 4,265,252 A | 5/1981 | Chubbuck et al. | |
| 4,281,666 A | 8/1981 | Cosman | |
| 4,281,667 A | 8/1981 | Cosman | |
| 4,340,038 A | 7/1982 | Mc Kean | |
| 4,354,506 A | 10/1982 | Sakaguchi et al. | |
| 4,361,153 A | 11/1982 | Slocum et al. | |
| 4,378,809 A | 4/1983 | Cosman | |
| 4,385,636 A | 5/1983 | Cosman | |
| 4,407,296 A | 10/1983 | Anderson | |
| 4,471,786 A | 9/1984 | Inagaki et al. | |
| 4,481,950 A | 11/1984 | Duggan | |
| 4,494,950 A | 1/1985 | Fischell | |
| 4,519,401 A | 5/1985 | Ko et al. | |
| 4,556,061 A | 12/1985 | Barreras et al. | |
| 4,593,703 A | 6/1986 | Cosman | |
| 4,596,255 A | 6/1986 | Snell et al. | |
| 4,614,192 A | 9/1986 | Imran et al. | |
| 4,616,640 A | 10/1986 | Kaali et al. | |
| 4,651,740 A | 3/1987 | Schroeppel | |
| 4,653,508 A | 3/1987 | Cosman | |
| 4,660,568 A | 4/1987 | Cosman | |
| 4,676,255 A | 6/1987 | Cosman | |
| 4,677,985 A | 7/1987 | Bro et al. | |
| 4,708,127 A | 11/1987 | Abdelghani | |
| 4,719,919 A | 1/1988 | Moran et al. | |
| 4,791,915 A | 12/1988 | Barsotti et al. | |
| 4,791,936 A | 12/1988 | Snell et al. | |
| 4,793,825 A | 12/1988 | Benjamin et al. | |
| 4,869,251 A | 9/1989 | Lekholm et al. | |
| 4,885,002 A | 12/1989 | Watanabe et al. | |
| 4,911,217 A | 3/1990 | Dunn et al. | |
| 4,918,736 A | 4/1990 | Bordewijk | |
| 5,074,310 A | 12/1991 | Mick | |
| 5,113,859 A | 5/1992 | Funke | |
| 5,117,835 A | 6/1992 | Mick | |
| 5,160,870 A | 11/1992 | Carson et al. | |
| 5,168,869 A | 12/1992 | Chirife | |
| 5,184,605 A | 2/1993 | Grzeszykowski | |
| 5,218,861 A | 6/1993 | Brown et al. | |
| 5,279,292 A | 1/1994 | Baumann et al. | |
| 5,291,899 A | 3/1994 | Watanabe et al. | |
| 5,381,067 A | 1/1995 | Greenstein et al. | |
| 5,423,334 A | 6/1995 | Jordan | |
| 5,433,736 A | 7/1995 | Nilsson | |
| 5,445,150 A | 8/1995 | Dumoulin et al. | |
| 5,495,453 A | 2/1996 | Wojciechowski et al. | |
| 5,562,621 A | 10/1996 | Claude et al. | |
| 5,619,997 A | 4/1997 | Kaplan | |
| 5,620,475 A | 4/1997 | Magnusson | |
| 5,704,352 A | 1/1998 | Tremblay et al. | |
| 5,704,366 A | 1/1998 | Tacklind et al. | |
| 5,712,917 A | 1/1998 | Offutt | |
| 5,721,886 A | 2/1998 | Miller | |
| 5,724,985 A | 3/1998 | Snell et al. | |
| 5,743,267 A | 4/1998 | Nikolic et al. | |
| 5,749,909 A | 5/1998 | Schroeppel et al. | |
| 5,757,104 A | 5/1998 | Getman et al. | |
| 5,759,199 A | 6/1998 | Snell et al. | |
| 5,800,478 A | 9/1998 | Chen et al. | |
| 5,807,258 A | 9/1998 | Cimochowski et al. | |
| 5,814,089 A | 9/1998 | Stokes et al. | |
| 5,833,603 A | 11/1998 | Kovacs et al. | |
| 5,861,018 A | 1/1999 | Feierbach | |
| 5,891,180 A | 4/1999 | Greeninger et al. | |
| 5,904,708 A | 5/1999 | Goedeke | |
| 5,925,001 A | 7/1999 | Hoyt et al. | |
| 5,935,078 A | 8/1999 | Feierbach | |
| 5,957,861 A | 9/1999 | Combs et al. | |
| 5,967,989 A | 10/1999 | Cimochowski et al. | |
| 6,015,387 A | 1/2000 | Schwartz et al. | |
| 6,030,374 A | 2/2000 | McDaniel | |
| 6,070,103 A | 5/2000 | Ogden | |
| 6,140,740 A | 10/2000 | Porat et al. | |
| 6,141,588 A | 10/2000 | Cox | |
| 6,162,238 A | 12/2000 | Kaplan et al. | |
| 6,164,284 A | 12/2000 | Schulman et al. | |
| 6,167,303 A | 12/2000 | Thompson | |
| 6,170,488 B1 | 1/2001 | Spillman, Jr. et al. | |
| 6,176,840 B1 | 1/2001 | Nishimura et al. | |
| 6,183,426 B1 | 2/2001 | Akisada et al. | |
| 6,185,452 B1 | 2/2001 | Schulman et al. | |
| 6,185,454 B1 | 2/2001 | Thompson | |
| 6,185,460 B1 | 2/2001 | Thompson | |
| 6,198,963 B1 | 3/2001 | Haim et al. | |
| 6,198,965 B1 | 3/2001 | Penner et al. | |
| 6,198,971 B1 | 3/2001 | Leysieffer | |
| 6,200,265 B1 | 3/2001 | Walsh et al. | |
| 6,236,889 B1 | 5/2001 | Soykan et al. | |
| 6,237,398 B1 | 5/2001 | Porat et al. | |
| 6,248,080 B1 | 6/2001 | Miesel et al. | |
| 6,259,951 B1 | 7/2001 | Kuzma et al. | |
| 6,260,152 B1 | 7/2001 | Cole et al. | |
| 6,261,249 B1 | 7/2001 | Talish et al. | |
| 6,277,078 B1 | 8/2001 | Porat et al. | |
| 6,315,721 B2 | 11/2001 | Schulman et al. | |
| 6,427,088 B1 | 7/2002 | Bowman et al. | |
| 6,431,175 B1 | 8/2002 | Penner et al. | |
| 6,432,050 B1 | 8/2002 | Porat et al. | |
| 6,442,413 B1 | 8/2002 | Silver | |
| 6,442,433 B1 | 8/2002 | Linberg | |
| 6,472,991 B1 | 10/2002 | Schulman et al. | |
| 6,473,638 B2 | 10/2002 | Ferek-Petric | |
| 6,564,807 B1 | 5/2003 | Schulman et al. | |
| 6,577,899 B2 | 6/2003 | Lebel et al. | |
| 6,584,352 B2 | 6/2003 | Combs et al. | |
| 6,607,485 B2 | 8/2003 | Bardy | |
| 6,628,989 B1 | 9/2003 | Penner et al. | |
| 6,644,322 B2 | 11/2003 | Webb | |
| 6,664,763 B2 | 12/2003 | Echarri et al. | |
| 6,671,552 B2 | 12/2003 | Merritt et al. | |
| 6,676,601 B1 | 1/2004 | Lacoste | |
| 6,689,091 B2 | 2/2004 | Bui et al. | |
| 6,712,772 B2 | 3/2004 | Cohen et al. | |
| 6,731,976 B2 | 5/2004 | Penn et al. | |
| 6,735,532 B2 | 5/2004 | Freed et al. | |
| 6,754,538 B2 | 6/2004 | Linberg | |
| 6,764,446 B2 | 7/2004 | Wolinsky et al. | |
| 6,788,973 B2 | 9/2004 | Davis et al. | |
| 6,790,187 B2 | 9/2004 | Thompson et al. | |
| 6,799,280 B1 | 9/2004 | Edenfield et al. | |
| 6,804,557 B1 | 10/2004 | Kroll | |
| 6,826,430 B2 | 11/2004 | Faltys et al. | |
| 6,855,115 B2 | 2/2005 | Fonseca et al. | |
| 6,873,869 B2 | 3/2005 | Fischer | |
| 6,960,801 B2 | 11/2005 | Lung | |
| 6,970,037 B2 | 11/2005 | Sakhuja et al. | |
| 6,978,181 B1 | 12/2005 | Snell | |
| 6,985,088 B2 | 1/2006 | Goetz et al. | |
| 6,985,773 B2 | 1/2006 | Von Arx et al. | |
| 6,988,215 B2 | 1/2006 | Splett et al. | |
| 6,993,393 B2 | 1/2006 | Von Arx et al. | |
| 7,003,349 B1 | 2/2006 | Andersson et al. | |
| 7,013,178 B2 | 3/2006 | Reinke et al. | |
| 7,024,248 B2 | 4/2006 | Penner et al. | |
| 7,027,871 B2 | 4/2006 | Burnes et al. | |
| 7,027,872 B2 | 4/2006 | Thompson | |
| 7,035,684 B2 | 4/2006 | Lee | |
| 7,060,030 B2 | 6/2006 | Von Arx et al. | |
| 7,082,334 B2 | 7/2006 | Boute et al. | |
| 7,096,068 B2 | 8/2006 | Mass et al. | |
| 7,123,964 B2 | 10/2006 | Betzold et al. | |
| 7,198,603 B2 | 4/2007 | Penner et al. | |
| 7,203,551 B2 | 4/2007 | Houben et al. | |
| 7,209,790 B2 | 4/2007 | Thompson et al. | |
| 7,212,133 B2 | 5/2007 | Goetz et al. | |
| 7,236,821 B2 | 6/2007 | Cates et al. | |
| 7,273,457 B2 | 9/2007 | Penner | |
| 7,283,874 B2 | 10/2007 | Penner | |
| 7,286,872 B2 | 10/2007 | Kramer et al. | |
| 7,319,903 B2 | 1/2008 | Bange et al. | |
| 7,335,161 B2 | 2/2008 | Von Arx et al. | |
| 7,353,063 B2 | 4/2008 | Simms, Jr. | |
| 7,469,161 B1 | 12/2008 | Gandhi et al. | |
| 7,479,108 B2 | 1/2009 | Rini et al. | |
| 7,617,001 B2 | 11/2009 | Penner et al. | |
| 7,650,185 B2 | 1/2010 | Maile et al. | |
| 7,756,587 B2 | 7/2010 | Penner et al. | |

| | | |
|---|---|---|
| 2001/0025139 A1 | 9/2001 | Pearlman |
| 2002/0065540 A1 | 5/2002 | Lebel et al. |
| 2002/0077673 A1 | 6/2002 | Penner et al. |
| 2002/0151770 A1 | 10/2002 | Noll, III et al. |
| 2002/0177782 A1* | 11/2002 | Penner .................. 600/485 |
| 2002/0190274 A1 | 12/2002 | Lung |
| 2003/0114897 A1 | 6/2003 | Von Arx et al. |
| 2003/0189488 A1 | 10/2003 | Forcier et al. |
| 2003/0212441 A1 | 11/2003 | Starkweather et al. |
| 2004/0039424 A1 | 2/2004 | Merritt et al. |
| 2004/0133092 A1 | 7/2004 | Kain |
| 2004/0152999 A1 | 8/2004 | Cohen et al. |
| 2004/0172083 A1* | 9/2004 | Penner .................. 607/35 |
| 2004/0210141 A1 | 10/2004 | Miller |
| 2005/0052223 A1 | 3/2005 | Sakhuja et al. |
| 2005/0113705 A1 | 5/2005 | Fischell et al. |
| 2005/0159785 A1 | 7/2005 | Rueter |
| 2005/0159789 A1 | 7/2005 | Brockway et al. |
| 2005/0203444 A1 | 9/2005 | Schonenberger et al. |
| 2005/0288727 A1 | 12/2005 | Penner |
| 2006/0009818 A1 | 1/2006 | Von Arx et al. |
| 2006/0020307 A1 | 1/2006 | Davis et al. |
| 2006/0025834 A1 | 2/2006 | Von Arx et al. |
| 2006/0031378 A1 | 2/2006 | Vallapureddy et al. |
| 2006/0041287 A1 | 2/2006 | Dewing et al. |
| 2006/0041288 A1 | 2/2006 | Dewing et al. |
| 2006/0058627 A1 | 3/2006 | Flaherty et al. |
| 2006/0064134 A1 | 3/2006 | Mazar et al. |
| 2006/0064135 A1 | 3/2006 | Brockway |
| 2006/0064142 A1 | 3/2006 | Chavan et al. |
| 2006/0085039 A1 | 4/2006 | Hastings et al. |
| 2006/0122667 A1 | 6/2006 | Chavan et al. |
| 2006/0142819 A1 | 6/2006 | Penner et al. |
| 2006/0149329 A1 | 7/2006 | Penner |
| 2007/0010742 A1 | 1/2007 | Torp et al. |
| 2007/0142728 A1 | 6/2007 | Penner et al. |
| 2007/0150014 A1 | 6/2007 | Kramer et al. |
| 2007/0162090 A1 | 7/2007 | Penner |
| 2007/0179549 A1 | 8/2007 | Russie |
| 2007/0250126 A1 | 10/2007 | Maile et al. |
| 2008/0015421 A1 | 1/2008 | Penner |
| 2008/0071178 A1 | 3/2008 | Greenland et al. |
| 2008/0103553 A1 | 5/2008 | Penner et al. |
| 2008/0108915 A1 | 5/2008 | Penner |
| 2008/0171941 A1 | 7/2008 | Huelskamp et al. |
| 2008/0195002 A1 | 8/2008 | Thompson et al. |
| 2009/0312650 A1 | 12/2009 | Maile et al. |
| 2009/0326609 A1 | 12/2009 | Doron |
| 2010/0023091 A1 | 1/2010 | Stahmann et al. |
| 2010/0106028 A1 | 4/2010 | Penner et al. |
| 2011/0160804 A1 | 6/2011 | Penner |

FOREIGN PATENT DOCUMENTS

| | | |
|---|---|---|
| EP | 0 928 598 | 12/1998 |
| EP | 1962557 | 8/2008 |
| JP | 10-505529 | 6/1998 |
| JP | 2004-511313 | 4/2004 |
| JP | 2004537347 | 12/2004 |
| JP | 2005521528 | 7/2005 |
| WO | WO88/02250 | 4/1988 |
| WO | WO 9626673 A1 | 9/1996 |
| WO | WO98/43338 | 10/1998 |
| WO | WO99/34453 | 7/1999 |
| WO | WO00/47109 | 8/2000 |
| WO | WO01/28627 | 4/2001 |
| WO | WO01/74278 | 10/2001 |
| WO | WO 01-76687 | 10/2001 |
| WO | WO01/97907 | 12/2001 |
| WO | WO02/03347 | 1/2002 |
| WO | 0232502 | 4/2002 |
| WO | WO 02089904 A1 | 11/2002 |
| WO | WO03/002243 | 1/2003 |
| WO | 03043688 | 5/2003 |
| WO | WO03/096889 | 11/2003 |
| WO | WO 2004-089465 | 10/2004 |
| WO | WO2005/009535 | 2/2005 |
| WO | WO2005/053786 | 6/2005 |
| WO | WO 2005-099816 | 10/2005 |
| WO | WO 2006-017615 | 2/2006 |
| WO | WO 2006-034183 | 3/2006 |
| WO | WO2006/060668 | 6/2006 |
| WO | WO2007/070794 | 6/2007 |
| WO | WO2007/080487 | 7/2007 |
| WO | WO2007/127696 | 11/2007 |

OTHER PUBLICATIONS

Ishiwara et al., "Current Status and Prospects of FET-Type Ferroelectric Memories," Journal of Semiconductor Technology and Science 1(1):Mar. 1-14, 2001.

International Search Report and Written Opinion of international application No. PCT/US2008/058134, mailed Aug. 26, 2008, 13 pp.

IEEE Transactions on Biomedical Engineering, vol. 42, No. 5, May 1995, Title: Data Transmission from an Implantable Biotelemeter by Load-Shift Keying Using Circuit Configuration Modulator, by Zhengnian Tang, Brian Smith, John H. Schild, and P. Hunter Peckham, pp. 524-528.

Neurosurgery Clinics of North America vol. 4, No. 4, Oct. 1993, Hydrocephalus, Title: The Treatment of Hydrocephalus by Paul M. Kanev, MD, and T.S. Park, MD., pp. 611-619.

Neurosurgery Clinics of North America, vol. 4, No. 4, Oct. 1993, Hydrocephalus, Title: Complications in Ventricular Cerebrospinal Fluid Shunting by Jeffrey P. Blount, MD, John A. Campbell, MD, and Stephen J. Haines, MD, pp. 633-656.

Neurosurgery Update II Vascular, Spinal, Pediatric, and Functional Neurosurgery, Published by McGraw-Hill, Inc., 1991, Editors Robert H. Wilkins, M.D., and Setti S. Rengachary, M.D., Title Shunt Complications by R. Michael Scott, pp. 300-319.

Neurosurgery, vol. 34, No. 5, May 1994, Concepts and Innovations, Title: A New Ventricular Catheter for the Prevention and Treatment of Proximal Obstruction in Cerebrospinal Fluid Shunts, by Enrique C.G. Ventureyra, M.D., F.R.C.S.(C)., F.A.C.S., Michael J. Higgins, M.D., pp. 924-926.

Neurosurgery, vol. 34, No. 6, Jun. 1994, Rapid Communication, Title: The Use of the Codman-Medos Programmable Hakim Valve in the Management of Patients with Hydroceplhalus: Illustrative Cases, by Peter McL. Black, M.D., Ph.D., Rodolfo Hakim, M.D., Nancy Olsen Bailey, R.N., B.S.N., M.B.A., pp. 1110-1113.

Pediatric Neurosurgery 2nd Edition, Surgery of the Developing Nervous System, Published by W.B. Saunders Company Harcourt Brace Jovanovich, Inc., 1989. Title: Treatment of Hydrocephalus by Harold L. Rekate, M.D.; Ventricular Shunts: Complications and Results by Robert L. McLaurin, M.D.; pp. 200-229.

* cited by examiner

BIASED ACOUSTIC SWITCH FOR IMPLANTABLE MEDICAL DEVICE

CROSS-REFERENCE TO RELATED APPLICATION

The present application claims priority under 35 U.S.C. §119 to U.S. Provisional Application No. 60/908,171, filed on Mar. 26, 2007 and entitled "BIASED ACOUSTIC SWITCH FOR IMPLANTABLE MEDICAL DEVICE," which is herein incorporated by reference in its entirety.

TECHNICAL FIELD

The present disclosure relates to implantable medical devices. More specifically, the present disclosure relates to devices, systems, and methods for selectively activating implantable medical devices.

BACKGROUND

Implantable medical devices (IMDs) such as pacemakers and implantable cardioverter defibrillators are utilized in monitoring and regulating various conditions within the body. An implantable cardioverter defibrillator, for example, may be utilized in cardiac rhythm management applications to monitor the rate and rhythm of the heart and for delivering various therapies such as cardiac pacing, cardiac defibrillation, and/or cardiac therapy. The implantable medical device can communicate with other medical devices implanted within the body tasked to sense various physiological parameters occurring within the body. For example, one or more remote sensors may be located deep within the body for monitoring parameters such as temperature, pressure, strain, fluid flow, chemical properties, electrical properties, magnetic properties, and the like. Based on the measurements received from the remote sensor, the implantable medical device may then deliver an appropriate treatment to the patient.

Communication between implantable medical devices and remote sensors is sometimes accomplished via an acoustic telemetry link. An acoustic transducer on the remote device can be configured to receive an acoustic signal transmitted by the implantable medical device, from another device inserted within the body, or from an external device located outside of the patient's body. The acoustic energy from the signal can be configured to establish an acoustic telemetry link that can be utilized for communicating between the devices, to energize or power the remote device, or both.

In some systems, an acoustic wake-up circuit can be used to transition the remote device from an inactive, low-power state into an active state. The acoustic wake-up circuit can be connected to an acoustic transducer, which converts an acoustic wake-up signal received into an electrical signal that can be passed along to the wake-up circuit. An example acoustic wake-up switch that can used in such systems is described in U.S. Pat. No. 6,628,989, entitled "Acoustic Switch and Apparatus and Methods For Using Acoustic Switches Within A Body," which is incorporated herein by reference in its entirety.

SUMMARY

The present disclosure relates to devices and methods for selectively activating implantable medical devices. A medical device in accordance with an illustrative embodiment includes an energy storage device, an acoustic transducer configured to convert an acoustic signal into an electrical signal, a signal detector configured to generate a trigger signal when the electrical signal exceeds a specific threshold established by a biasing element, a control circuit, and an activation/deactivation switch configured to switch the medical device between an inactive state and an active state.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
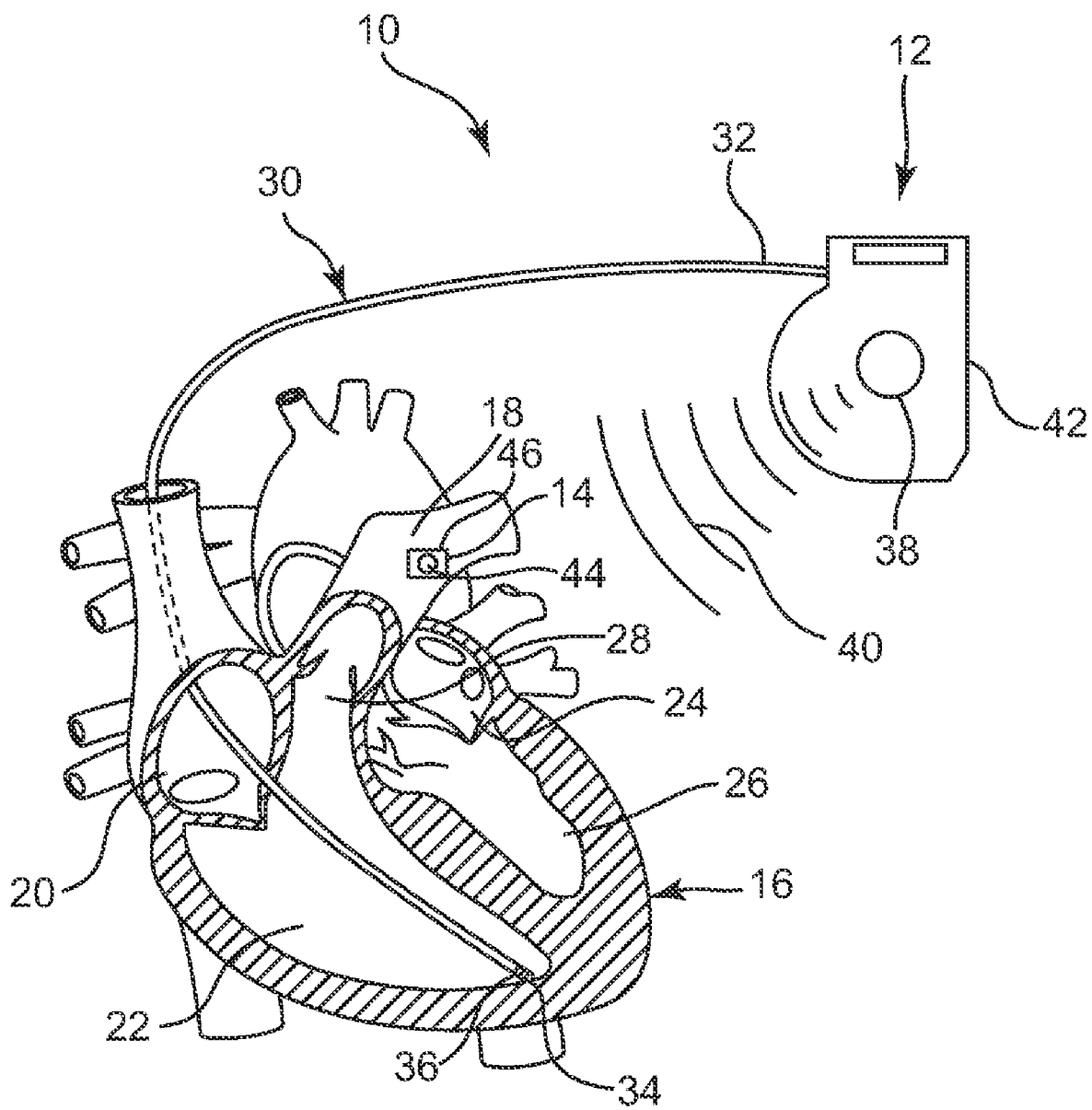
FIG. 1 is a schematic diagram showing an illustrative system for communicating with and/or powering one or more remote devices within the body of a patient.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of an illustrative system 10 for communicating with and/or powering one or more remote devices located within the body of a patient. In the embodiment of FIG. 1, the system 10 is a cardiac rhythm management system including a pulse generator 12 implanted within the body at a location below the patient's skin, and a remote sensor 14 implanted deeply within the patient's body such as in one of the arteries or ventricles of the patient's heart 16 or in one of the pulmonary arteries such as the main pulmonary artery 18, as shown. The heart 16 includes a right atrium 20, a right ventricle 22, a left atrium 24, and a left ventricle 26. The right ventricle 22 includes an outflow tract 28, which leads to the main pulmonary artery 18. While the illustrative embodiment of FIG. 1 includes a pulse generator 12 in communication with a remote sensor 14, in other embodiments the system 10 may employ other medical devices located inside or outside of the patient's body to communicate with the sensor 14.

The pulse generator 12 can be implanted subcutaneously within the body, typically at a location such as in the patient's chest or abdomen, although other implantation locations are possible. In the illustrative system 10 depicted, the pulse generator 12 is coupled to a lead 30 deployed in the patient's heart 16. A proximal portion 32 of the lead 30 can be coupled to or formed integrally with the pulse generator 12. A distal portion 34 of the lead 30, in turn, can be implanted at a desired location in or near the heart 16 such as the right ventricle 22, as shown. In use, an exposed electrode 36 on the distal portion 34 of the lead 30 may provide therapy to the patient in the form of an electrical current to the heart 16.

Although the illustrative system 10 depicts only a single lead 30 inserted into the patient's heart 16, the system 10 may include multiple leads so as to electrically stimulate other areas of the heart 16. In some embodiments, for example, the distal portion of a second lead (not shown) may be implanted in the right atrium 20 for providing electrical stimulation to the atrium 20. In addition, or in lieu, another lead may be implanted in or near the left side of the heart 16 (e.g., in the coronary veins) to stimulate the left side of the heart 16. Other types of leads such as epicardial leads may also be utilized in addition to, or in lieu of, the lead 30 depicted in FIG. 1.

During operation, the lead 30 can be configured to convey electrical signals between the pulse generator 12 and the heart 16. In those embodiments where the pulse generator 12 is a pacemaker, for example, the lead 30 can be utilized to deliver electrical therapeutic stimulus for pacing the heart 16. In those embodiments where the pulse generator 12 is an implantable cardiac defibrillator, the lead 30 can be utilized to provide electric shocks to the heart 16 in response to an event such as tachycardia or bradycardia. In some embodiments, the pulse generator 12 includes both pacing and defibrillation capabilities.

The remote 14 can be configured to perform one or more designated functions, including the sensing of physiological parameters within the body. Example physiological parameters that can be measured using the sensor 14, include but are not limited to, blood pressure, blood flow, temperature, and strain. Various electrical, chemical and/or magnetic properties may also be sensed within the body via the sensor 14. The specific configuration and function of the sensor 14 will typically vary depending on the particular therapeutic needs of the patient. In one illustrative embodiment, for example, the sensor 14 is a pressure sensor that can be implanted at a location deep within the body such as the main pulmonary artery 18 or a branch of the main pulmonary artery 18 (e.g., in the right or left pulmonary artery 18). An illustrative pressure sensor suitable for use in sensing mechanical activity within the body is described, for example, in U.S. Pat. No. 6,764,446, entitled "Implantable Pressure Sensors and Methods for Making and Using Them," which is incorporated herein by reference in its entirety. In other embodiments, however, the sensor 14 can be implanted at other locations within the body, and can be configured to measure other parameters. Examples of other implantation locations can include, but are not limited to, the right atrium 20, the right ventricle 22, the left atrium 24, the left ventricle 26, or the coronary arteries (not shown). An example sensor that can be anchored within the body is described in U.S. patent application Ser. No. 11/855,725, now issued to U.S. Pat. No. 8,057,399, issued on Nov. 11, 2005, entitled "Anchor for an Implantable Sensor," which is incorporated herein by reference in its entirety.

The remote sensor 14 can be used in conjunction with the pulse generator 12 and/or other medical devices to optimize pacing and/or defibrillation therapy, to predict decompensation of a heart failure patient, or to provide other monitoring and/or therapy functions. In certain embodiments, for example, the sensor 14 can be utilized in conjunction with an ICD to provide cardiac defibrillation to the patient as needed. Other devices such as a pulmonary sound sensor, satellite pacing device, or other such sensing and/or therapy-delivering device may also be used in conjunction with the pulse generator 12 and sensor 14.

In some embodiments, an acoustic telemetry link may be established to permit wireless communications between the pulse generator 12 and the sensor 14. In the illustrative system 10 of FIG. 1, for example, the pulse generator 12 includes an acoustic transducer 38 adapted to transmit an acoustic wave 40 within the body. In some embodiments, the acoustic transducer 38 is coupled to an interior portion of the can 42 that encloses various components of the pulse generator 12. In other embodiments, the acoustic transducer 38 is located outside of the can 42, or is coupled to the pulse generator 12 through a feedthrough provided on the can 42. An example acoustic transducer that can be used in implantable devices is described in U.S. Pat. No. 6,140,740, entitled "Piezoelectric Transducer," which is expressly incorporated herein by reference in its entirety.

An acoustic transducer 44 coupled to the housing 46 of the sensor 14 is configured to receive the acoustic wave 40, which as discussed further herein is used to activate the sensor 14 from a low-power, inactive state to an active, energized state. In one embodiment, for example, the acoustic wave 40 can be used to wake-up the sensor 14 from an initial, low-power state to an active state to take one or more measurements within the body and then transmit those measurements to the pulse generator 12, to another implanted medical device, and/or to an external medical device or caregiver server. In some embodiments, the acoustic wave 40 is used to provide power to the sensor 14 and/or to recharge an energy source within the sensor 14 such as a rechargeable battery or power capacitor. In some embodiments, the acoustic signal 40 provides acoustical energy that can be converted into therapeutic energy to provide therapy to the patient, if desired.

Figure 2:
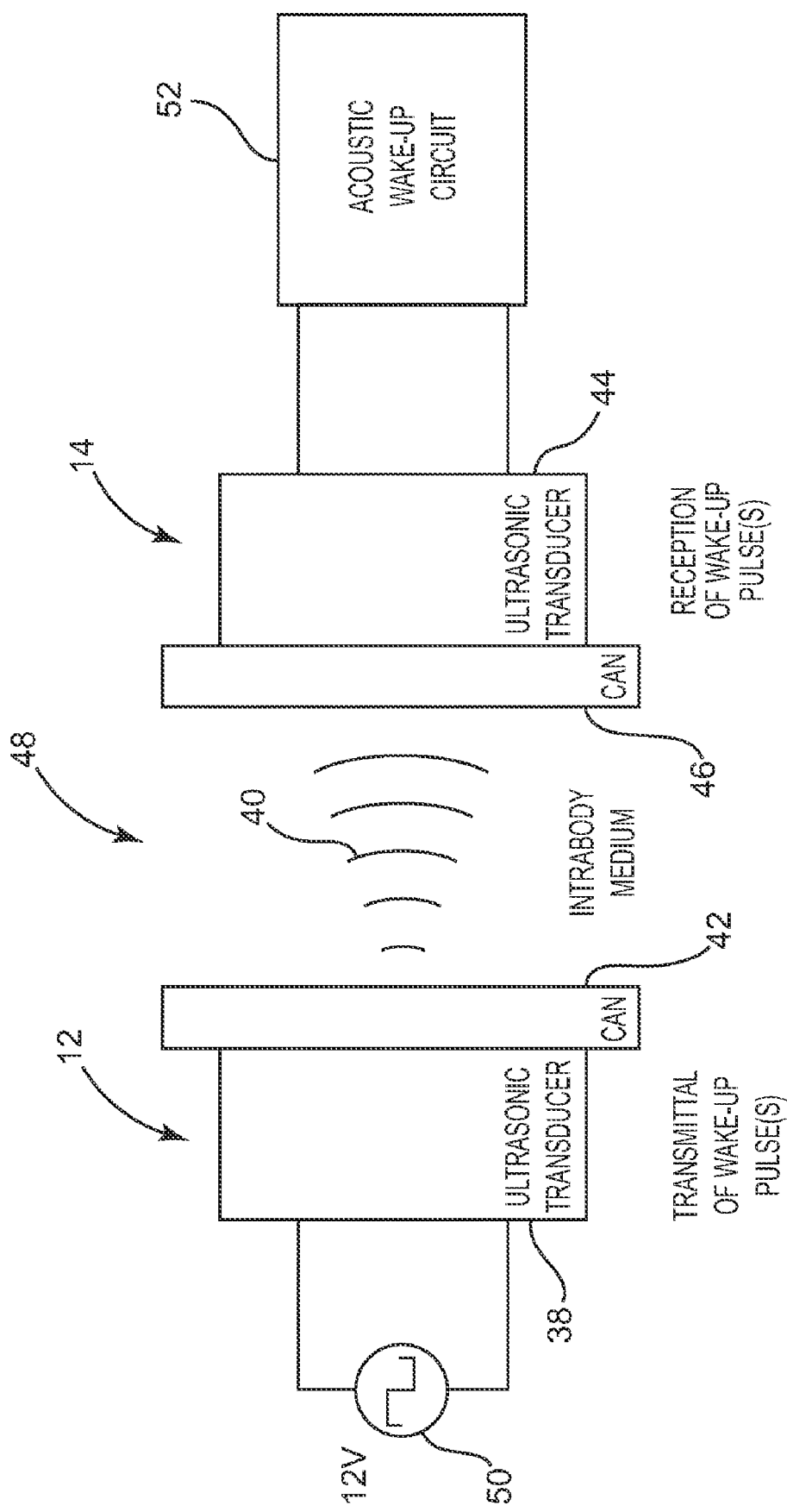
FIG. 2 is a schematic diagram showing an illustrative method of transmitting an acoustic wake-up signal to an acoustic wake-up circuit.

FIG. 2 is a schematic diagram showing an illustrative method 48 for providing an acoustic wake-up signal to switch the remote sensor 14 of FIG. 1 between an inactive, sleep state to an active, energized state to initiate communications back and forth between the sensor 14 and the pulse generator 12. As shown in FIG. 2, the pulse generator 12 generates an acoustic wake-up signal 50 for driving the acoustic transducer 38. In certain embodiments, the acoustic wake-up signal 50 can be used to activate the remote sensor 14 from a low-power, inactive state to an active, energized state to initiate communications back and forth between the sensor 14 and the pulse generator 12 and/or one or more other devices located inside or outside of the patient's body. In those embodiments where the sensor 14 comprises a pressure sensor implanted in or near the heart, for example, the acoustic wake-up signal 50 can be used to activate the sensor 14 and take pressure readings that can be used by the pulse generator 12 or another device in communication with the sensor 14 to predict heart decompensation within the patient. Other applications, however, are possible.

Upon excitation from the wake-up signal 50, the acoustic transducer 38 for the pulse generator 12 transmits an acoustic pulse 40 or series of pulses 40 through the body. The acoustic transducer 44 for the sensor 14 receives these acoustic pulses 40, which are then converted by the sensor 14 into an electrical signal. The electrical signal generated by the acoustic transducer 44 is then fed to an acoustic wake-up circuit 52 within the sensor 14, which as discussed in greater detail herein, can be used to either activate or deactivate the sensor 14.

During transmission of the acoustic pulses 40 through the body, absorption and spreading of the acoustic energy within the body tissue results in the attenuation of the acoustic energy received by the sensor 14. The attenuation is mostly due to spreading loss resulting from the acoustic energy dispensing within the body volume as well as absorption losses in the intrabody medium and reflection losses at the boundaries of the intrabody medium such as at the interface between different tissue types (e.g., between soft tissue and bone) where they may be an abrupt change in acoustic impedance. The amount of attenuation loss occurring within the body is dependent on several factors, including the physical anatomy between the pulse generator 12 and the sensor 14, the frequency of the acoustic transmission, possible directivities of the acoustic transducers 38,44, as well as other factors.

As a result of the acoustic losses occurring in the intrabody medium and at the medium interface, the acoustic energy received by the acoustic transducer 44 is significantly lower than that emitted by the transmitting acoustic transducer 38. This may be partially offset by using a high sensitivity receiving transducer 44, however the voltage of the electrical signal produced by the receiving acoustic transducer 44 is typically less than the voltage signal 50 applied to the transmitting acoustic transducer 38. By way of example and not limitation, a piezoelectric transducer 38 for the pulse generator 12 may be capable of producing an acoustic pressure of 100 Pa per 1 Volt of applied pressure, at a distance of about 25 cm from the transmitter. A 12V square wave excitation signal 50 applied to the acoustic transducer 38 thus produces an acoustic pulse 40 having a pressure of 1200 Pa at 25 cm separation. A 20 dB loss due to possible additional attenuation of the acoustic pulse 40 within the body will thus result in a 120 Pa acoustic signal received by the remote sensor transducer 44. Assuming a 1.5 mV/Pa sensitivity for the sensor 14, the resultant voltage produced from the conversion is 180 mV.

Figure 3:
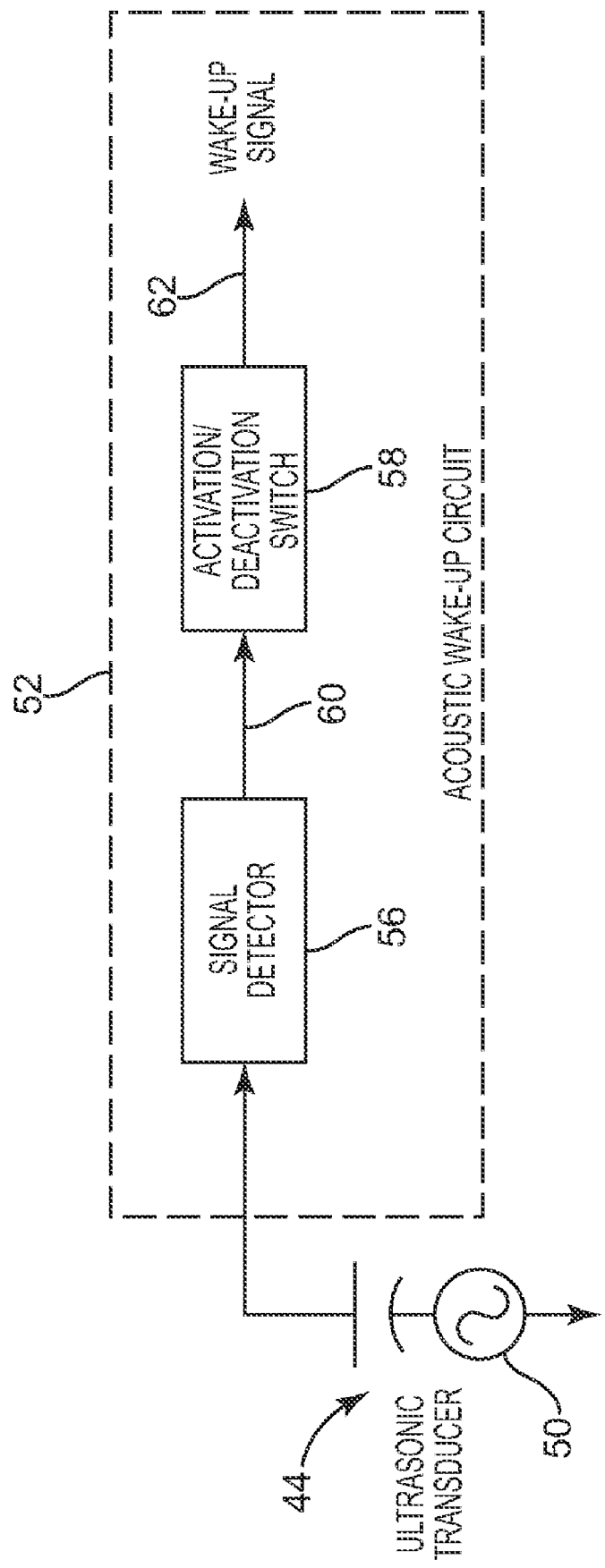
FIG. 3 is a schematic diagram showing an illustrative acoustic wake-up circuit.

FIG. 3 is a schematic diagram showing an acoustic wake-up circuit 52 in accordance with an illustrative embodiment. As shown in FIG. 3, the acoustic wake-up circuit 52 includes a signal detector 56 and an activation/deactivation switch 58 such as a latch. The signal detector 56 outputs an electrical signal 60 based on the amplitude of the incoming electrical signal produced by the transducer 44, which is a function of the sensitivity of the transducer 44. For piezoelectric transducers, the sensitivity of the transducer 44 is dependent upon the size of the transducer 44, its resonance characteristics, as well as other electrical and mechanical properties.

In some applications, it is desirable that the acoustic wake-up circuit 52 have a low wake-up threshold and lower power consumption. A low wake-up threshold is desired since a lower amplitude wake-up pulse can be generated with less energy in comparison to a large amplitude wake-up pulse, resulting in lower power consumption by the pulse generator transducer 42. In addition, a lower amplitude wake-up pulse can be generated using a simpler circuit and transducer configuration. The minimum threshold required to actuate the acoustic wake-up circuit 52 is typically selected so as to prevent the circuit 52 from inadvertently triggering the sensor 14 upon the reception of ambient acoustic noises as well as RF energy or other energy received by the transducer 44.

If the incoming acoustic signal 40 exceeds the minimum threshold of the signal detector 56, the signal detector 56 outputs an electrical signal 60 that causes the activation/deactivation switch 58 to switch its state. Examples of activation/deactivation switches that can be utilized include, but are not limited, to SR latches (e.g., cross-coupled NOR gates, cross-coupled NAND gates), D-latches, and flip-flops (e.g., master-slave flip-flops, JK flip flops). Depending on the previous state set by the activation/deactivation switch 58, the activation/deactivation switch 58 may output a wake-up signal 62 (or alternatively a power-down signal) to the control/processing circuitry of the sensor 14, causing the sensor 14 to switch states between either an inactive, low-power state or an active, energized state. If, for example, the activation/deactivation switch 58 was previously set to an inactive or sleep state, the reception of the electrical signal 60 outputted by the signal detector 56 causes the activation/deactivation switch 58 to switch its state and transmit a wake-up signal 62 that activates the sensor 14 to take sensor measurements within the body and/or to transmit sensor measurements back to the pulse generator 12 or other internal or external medical device. The activation/deactivation switch 58 holds the wake-up signal 62 in its asserted state until the system resets the activation/deactivation switch 58 just prior to returning to its inactive, low-power state.

Figure 4:
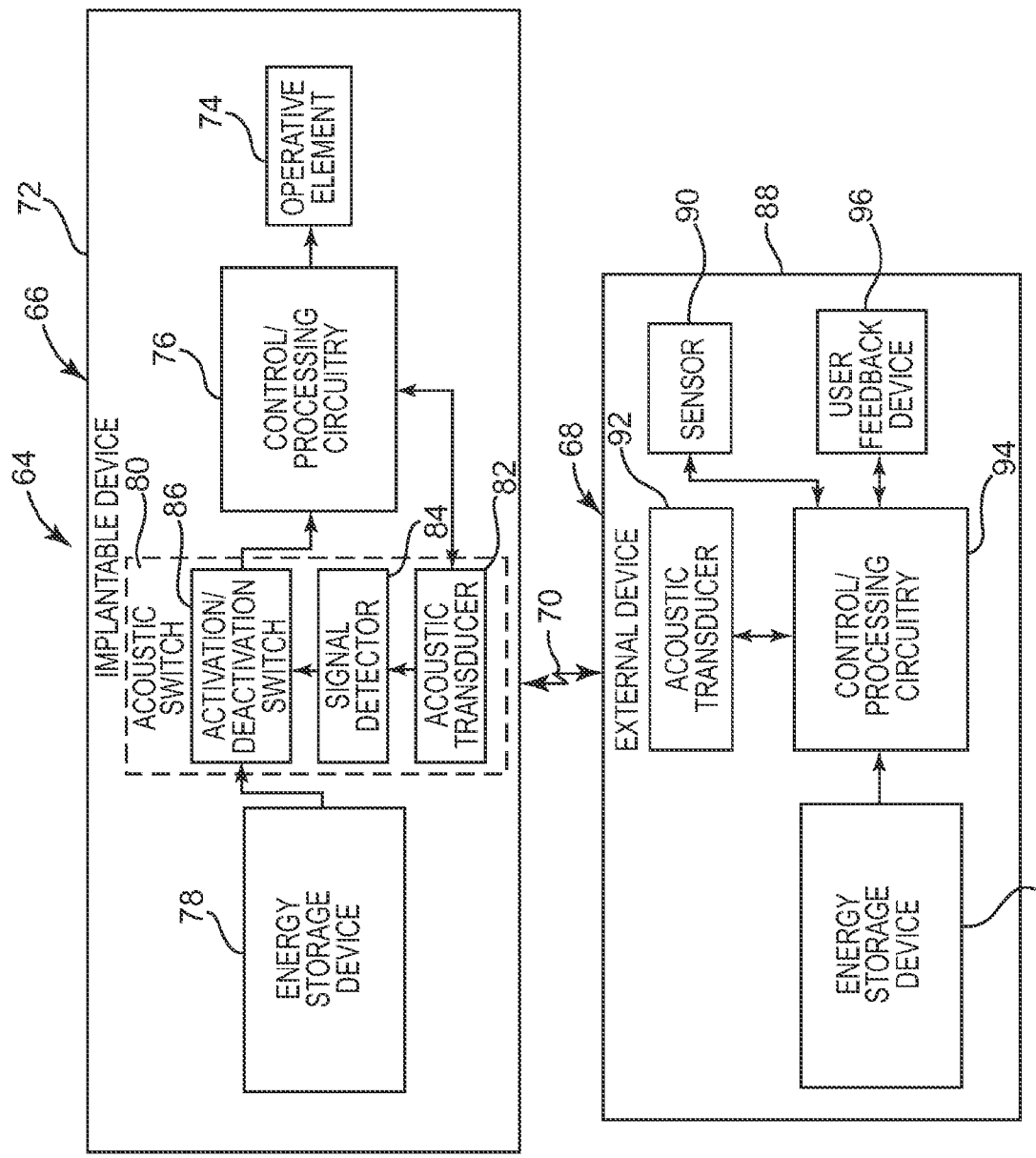
FIG. 4 is a schematic diagram showing an implantable system in accordance with an illustrative embodiment.

FIG. 4 is a schematic diagram showing an implantable system 64 in accordance with an illustrative embodiment. In the embodiment of FIG. 4, the system 64 includes an implantable medical device 66, which is configured for acquiring physiological information from a patient and/or providing therapy to the patient, and an external attachable device 68 configured for interacting with the implantable device 66 via a wireless link 70. For example, the external device 68 may wirelessly receive physiological information from the implantable device 66 and/or may wirelessly transmit therapeutic commands to the implantable device 66. In some embodiments, another implantable medical device (not shown) may wirelessly interact with the implantable device 66 either directly or indirectly via the external device 68 in the manner described in U.S. patent application Ser. No. 11/373,005, entitled "Body Attachable Unit In Wireless Communication With Implantable Devices," which is expressly incorporated herein by reference in its entirety. In some embodiments, the implantable system 64 may comprise an external auxiliary computing device, e.g., a desktop or portable computer, and/or a caregiver server or database (not shown).

The implantable device 66 can be selectively placed between an active state, during which the implantable device 66 expends energy to perform the intended medical function of the implantable device 66, and a standby state, during which the implantable device 66 is not currently performing its intended medical function and most or all of the energy-consuming circuitry is powered off. The implantable device 66 remains in the standby state until awoken to the active state by the external device 68. In some embodiments, and as discussed previously, the external device 68 is capable of transmitting an activation or wake-up command or signal to activate the implantable device 66. The external device 68 can also be configured to transmit a sleep command or signal that deactivates the implantable device 66. In some embodiments, the implantable device 66 may automatically deactivate after a certain period of time has elapsed or after a particular medical function has been performed.

In some embodiments, the implantable device 66 is configured for implantation deep within the tissue of the patient, e.g., in or near the heart or adjacent anatomical structures. The external device 68 wirelessly communicates with the implantable device 66 using acoustic energy (e.g., at a relatively low frequency of 40 kHz), and in particular, by transmitting and receiving acoustic energy through the tissue. In some embodiments, the external device 68 may wirelessly receive the physiological information from the implantable device 66 using acoustic energy and/or may transmit acoustic energy to control or operate the implantable device 66. The external device 68 may also transmit acoustic energy to charge the implantable device 66.

To ensure that the acoustic wireless link 70 between the implantable device 66 and external device 68 is reliable, the external device 68 is placed in close contact with the patient's skin. In certain embodiments, for example, the external device 68 is attached to the patient's wrist using a wrist band type attachment mechanism. Alternatively, and in other embodiments, the external device 68 is attachable to other parts of the patient body such as the patient's arm, neck, chest, thigh, or knee. The external device 68 can use any type of attachment mechanism, such as a strap, a patch, a belt, or any other means for assuring contact between at least part of the acoustically active component of the external device 68 and the patient's body. Further details regarding various means of securely attaching control devices to patients are provided in U.S. Pat. No. 7,283,874, entitled "Acoustically Powered Implantable Stimulating Device," which is expressly incorporated herein by reference in its entirety.

Alternatively, if implantation of the medical device 66 is superficial (e.g., just under the skin), the wireless link 70 may be non-acoustic such as via a radio frequency (RF) or inductive link. In this case, standard RF technology for wireless communication can be incorporated into the medical device 66 and external device 68 (e.g., Bluetooth® RF technology).

The structure of the implantable device 66 will now be described further with respect to FIG. 1. The diagnostic device 66 includes a casing 72, an operative element 74, control/processing circuitry 76, an energy storage device 78, and an acoustic switch 80, which includes an acoustic transducer 82, a signal detector 84 and an deactivation/activation switch component 86.

The casing 72 houses all of the internal components of the implantable device 66, is composed of a suitable biocompatible material, and is hermetically sealed to isolate the components from the environment outside of the diagnostic device 66. Further details regarding the construction of casings for implantable devices are described in U.S. Pat. No. 6,764,446, entitled "Implantable Pressure Sensors And Methods For Making And Using Them," which is expressly incorporated herein by reference in its entirety.

The operative element 74 may be any desired biosensor that generates a signal related to a measured physiological parameter. Such physiological parameters may include, but are not limited to, pressure, temperature, electrical impedance, position, strain, pH, blood flow, radiation level, glucose level, and the like. Additional sensors may be provided for the measurement of other physiological parameters, if desired. The operative element 74 or an additional operative element may also be any desired bioactuator that provides therapy to the patient, e.g., drug delivery or neurostimulation. Additional actuators may be provided if other modes of therapy are desired.

The control/processing circuitry 76 includes circuitry for activating or controlling the operative element 74. For example, if the operative element 74 is a biosensor, under control of the control/processing circuitry 76, physiological parameters sensed by the operative element 74 may be measured and the resulting physiological information wirelessly transmitted via the acoustic transducer 82 from the implantable device 66, either continuously or periodically, until the implantable device 66 is deactivated, or for a fixed predetermined time, as will be appreciated by those skilled in the art. If the operative element 74 is a bioactuator under control of the control/processing circuitry 76, therapy may be provided by the operative element 74 using a pre-programmed protocol.

The control/processing circuitry 76 may also include memory for storing information such as data received from the operative element 74 and/or commands for use internally. The control/processing circuitry 76 may include an oscillator or other circuitry for wirelessly transmitting acoustic signals to the patient attachable device 68 via the acoustic transducer 82, signal detection circuitry for wirelessly receiving acoustic signals from the patient attachable device 68 via the acoustic transducer 82, and/or a processor for analyzing, interpreting, and/or processing the received signals. The control/processing circuitry 76 may include a processor for analyzing, interpreting, and/or processing the signals received by the operative element 74 and the external device 68. The control/processing circuitry 76 can be configured as a digital signal processor (DSP), field programmable gate array (FPGA), application specific integrated circuit (ASIC)-compatible device such as a CoolRISC processor available from Xemics, or other programmable devices and/or any other hardware components or software modules for processing, analyzing, storing data, and controlling the operation of the implantable device 66.

The energy storage device 78 may be any of a variety of known devices such as a battery and/or a capacitor. In the illustrated embodiment of FIG. 1, the energy storage device 78 includes both a capacitor and a primary, non-rechargeable battery. In some embodiments, the energy storage device 78 is capable of storing electrical energy substantially indefinitely unless actively discharged. In addition, the energy storage device 78 may be capable of being charged from an external source, and in particular, from acoustic energy transmitted to the implantable device 66 from the external device 68 or inductively from another external device.

In response to an externally generated acoustic activation or wakeup signal, the acoustic switch 80 is configured to place the implantable device 66 from the standby state in which the conveyance of electrical current from the energy storage device 78 to the control/processing circuitry 76 or any other circuitry requiring electrical current to operate is substantially prevented, to the active state in which the conveyance of electrical current from the energy storage device 78 to the control/processing circuitry 76 or any other circuitry in the implantable device 66 requiring electrical current to operate is allowed. Notably, when the implantable device 66 is in the standby state, there is substantially no current consumption from the energy storage device 78, typically less than about 50 nA, and preferably less than 20 nA, and consequently, the implantable device 66 may remain in the standby state virtually indefinitely until activated. Thus, the implantable device 66 is more energy efficient and therefore requires a smaller energy storage device than implantable devices that continuously draw at least a small amount of current in their "passive" states to maintain active amplifiers, detectors, and the control circuit.

In some embodiments, the acoustic switch 80 is biased with a DC voltage so that the magnitude of the activation signal required to close the acoustic switch 80 is decreased. In response to the acoustic activation signal, the acoustic switch 80 internally generates a time-varying electrical signal, and in some embodiments an AC electrical signal. In certain embodiments, a DC voltage bias is added to close the acoustic switch 80, thereby enhancing the wake-up sensitivity of the implantable device 66. In order to achieve reliable switching, the AC electrical signal is generated at a voltage that, when combined with the DC voltage bias, is sufficient to close the acoustic switch 80.

In certain embodiments, the acoustic transducer 82 includes one or more piezoelectric transducer elements configured for transmitting and receiving acoustic signals. In some embodiments, the acoustic transducer 82 generates an electrical signal proportional to the magnitude of the acoustic signal wirelessly received from the external device 68, which is then conveyed to the control/processing circuitry 76 when the implantable device 66 is in the active state. Similarly, the acoustic transducer 82 generates an acoustic signal proportional to the magnitude of the electrical signal conveyed from the control/processing circuitry 76 when the implantable device 66 is in the active state, which is then wirelessly transmitted to the external device 68.

During the active state, the acoustic switch 80 is closed and the electrical signal bidirectionally passes between the acoustic transducer 82 and the control/processing circuitry 76 without any hindrance from the signal detector 84 and the deactivation/activation switch component 86. In some embodiments, the acoustic transducer 82 is coupled to the control/processing circuitry 76 in parallel with the signal detector 86 and the deactivation/activation switch component 86. In other embodiments, the acoustic transducer 82 is coupled to the control/processing circuitry 76 in series with the signal detector 84 and the deactivation/activation switch component 86. As discussed previously, an acoustical activation or wake-up signal can be used to activate the implantable device 66 when the implantable device 66 is in the standby state. When in the standby state, the electrical signal is not passed to the control/processing circuitry 76, but rather acts solely to close the acoustic switch 80.

In alternative embodiments, an electromagnetic or magnetic transducer (e.g., an antenna) is used in lieu of an acoustic transducer to establish a telemetry link. The antenna may take the form of a standard antenna for transmitting and receiving electromagnetic energy in the radio frequency (RF) spectrum or pulsed magnetic energy. In particular, the antenna generates an electrical signal proportional to the magnitude of a electromagnetic/magnetic signal wirelessly received from the external device 68, which is then conveyed to the control/processing circuitry 76 when the implantable device 66 is in the active state. Similarly, the antenna generates an electromagnetic/magnetic signal proportional to the magnitude of the electrical signal conveyed from the control/processing circuitry 76, which is then wirelessly transmitted to the external device 68 when the implantable device 66 is in the active state. The electrical signal generated by the antenna may be used to activate the implantable device 66 in the same manner as the electrical signal generated by the acoustic transducer 82 as discussed above.

The signal detector 84 is configured for generating an activation trigger signal to activate the implantable device 66 via the deactivation/activation switch component 86. The activation trigger signal is generated by the signal detector 84 when the AC electrical signal generated by the acoustic transducer 82 exceeds a specific voltage threshold, and in particular, when the voltage level of the AC electrical signal in combination with the DC bias voltage level exceeds the voltage threshold of the signal detector 84.

The deactivation/activation switch component 86 is the component through which current is delivered from the energy storage device 78 to the control/processing circuitry 76 when actuated. In response to the generation of the activation trigger signal by the signal detector 84, the switch component 86 is actuated to allow current to flow to the control/processing circuitry 76, thereby placing the implantable device 66 in the active state. The switch component 86 can also be actuated (e.g., by a control signal from the control/processing circuitry 76) to prevent current from flowing to the control/processing circuitry 76, thereby placing the implantable device 66 in the standby state.

In some embodiments, the switch component 86 may be further used to control other circuitry within the implantable device 66 such as to enable a regulated power supply or to transition the device 66 between the active state and standby state. For example, in some embodiments the activation signal by the signal detector 84 is used to enable a regulated power supply that powers the control/processing circuitry 76 instead of the circuitry 76 being in series with a switch on a power supply that is always present.

To activate the implantable device 66, one or more activation acoustic energy waves or signals can be transmitted from the external device 68 into the patient's body (e.g., in a direction towards the location of the implantable device 66) until the signal is received by the acoustic transducer 82. Upon excitation by the acoustic waves, the acoustic transducer 82 generates an electrical signal that causes the signal detector 84 to generate a trigger signal that is used to close, open, or otherwise activate the switch component 86. Further details regarding the general construction and function of acoustic switches are disclosed in U.S. Pat. No. 6,628,989, entitled "Acoustic Switch And Apparatus And Methods For Using Acoustic Switches Within The Body," which is expressly incorporated herein by reference in its entirety.

In certain embodiments, the external device 68 is a small portable, battery operated device. In the illustrative embodiment of FIG. 4, the external device 68 includes a casing 88, an on-board sensor 90, an acoustic transducer 92, a control/processing unit 94, an audio/visual user feedback device 96, and an energy storage device 98.

The casing 88 houses the components of the external device 68 and is comprised of a suitable material such as plastic. In some embodiments, the casing 88 is sized and shaped to be comfortably held or worn by the patient. The sensor 90 may be any desired sensor that generates a signal proportional to a measured parameter such as a barometric sensor. The external device 68 may include one or more additional sensors (not shown) such as an ECG electrode sensor, a systemic blood pressure sensor, a posture sensor, a global positioning sensor (GPS), an activity sensor, a temperature sensor, a timer and/or an oximeter.

In some embodiments, the acoustic transducer 92 is configured for both transmitting and receiving acoustic signals. The acoustic transducer 92 generates an electrical signal proportional to the magnitude of acoustic energy received by the acoustic transducer 92, which is then conveyed to the control/processing circuitry 94. In similar fashion, the acoustic transducer 92 generates an acoustic signal proportional to the magnitude of the electrical energy conveyed from the control/processing circuitry 94 to the acoustic transducer 92. An example of an acoustic transducer that can be used in small profile external units is disclosed in U.S. Pat. No. 11/287,557, now issued to U.S. Pat. No. 7,580,750, issued on Aug. 25, 2009, entitled "Implantable Medical Device with Integrated Acoustic Transducer," which is expressly incorporated herein by reference in its entirety. Alternatively, if communication with the implantable device 66 is accomplished via an electromagnetic or magnetic telemetry link, the external device 98 may alternatively include an antenna instead of an acoustic transducer.

The control/processing circuitry 94 includes circuitry for activating or controlling the sensor 90 and for receiving signals from the sensor 90. In some embodiments, the control/processing circuitry 94 may include an oscillator or other circuitry for wirelessly transmitting acoustic signals to the implantable device 66 via the acoustic transducer 92. The control/processing circuitry 94 can also include signal detection circuitry in some embodiments for wirelessly receiving acoustic signals from the implantable device 66 via the acoustic transducer 92 or from another acoustic transducer coupled to the external device 68.

In some embodiments, the control/processing circuitry 94 includes a processor for analyzing, interpreting, and/or processing the received signals, and a memory for storing the processed information and/or commands for use internally. The control/processing circuitry 94 can be configured as a digital signal processor (DSP), field programmable gate array (FPGA), application specific integrated circuit (ASIC)-compatible device such as a CoolRISC processor available from Xemics or other programmable devices, and/or any other hardware components or software modules for processing, analyzing, storing data, and controlling the operation of the external device 68.

The user feedback device 96 can include a screen for presenting a reading from the implantable device 66 or the on-board sensor 90 (e.g., for displaying pressure readings) to the patient, a speaker, and/or tactile feedback means. The energy storage device 98 may be any of a variety of known devices such as a battery and/or a capacitor. In some embodiments, the external device 68 includes an interface for connecting to the Internet, to a cell phone, and/or to other wired or wireless means for downloading or uploading information and programs, debugging data and upgrades. In some embodiments, this connection may also be used for charging the energy storage device 98.

Figure 5:
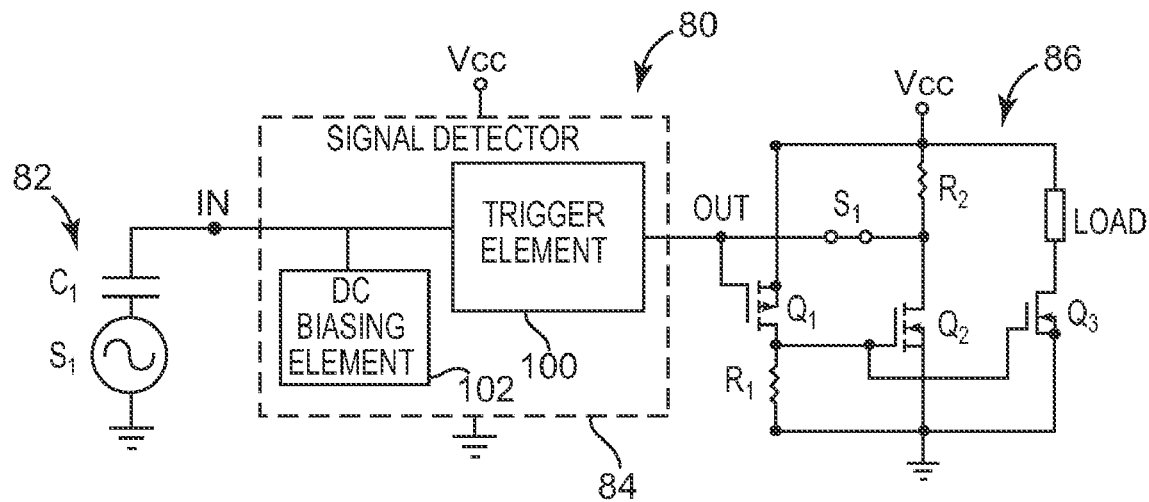
FIG. 5 is a circuit diagram showing an embodiment of an acoustic switch that can be used in the implantable system of FIG. 4.

FIG. 5 is a circuit diagram showing an illustrative embodiment of an acoustic switch that can be used in the implantable system of FIG. 4. As shown in FIG. 5, the acoustic transducer 82, when excited by an acoustic signal, can be modeled as a small signal sinusoidal source S1, which represents the AC electrical signal generated by the acoustic transducer 82, and a capacitor C1, which represents the intrinsic capacitance C1 of the transducer 82. The signal detector 84 comprises an input terminal IN coupled to the output of the acoustic transducer 82 for receiving the AC electrical signal, and an output terminal OUT coupled to the input of the deactivation/activation switch component 84 for applying an activation trigger signal. The signal detector 84 is powered by a supply voltage $V_{cc}$ derived from the energy storage device 78. The signal detector 84 can be functionally divided into a trigger element 100, which generates the activation trigger signal in response to the AC electrical signal, and a DC bias element 102 that provides a DC voltage bias to the input terminal IN.

The DC bias element 102 biases the trigger element 100 with the DC voltage level by applying the DC bias voltage at the input of the signal detector 84, thereby setting the specific voltage threshold at which the AC electrical signals cause the signal detector 84 to generate the activation trigger signal. As will be described in further detail below, the DC bias element 102 may either be incorporated within the trigger element 100 itself, or may be peripheral to the trigger element 100, and may either act directly or indirectly on the input of the signal detector 84. In use, the DC bias element 102 provides a DC bias voltage that is added to the AC electrical signal generated by the acoustic transducer 82, and thus reduces energy level of the acoustic signal necessary to generate the activation trigger signal.

The signal detector 84 is configured to generate the activation trigger signal in response to lower acoustic signal levels as compared to the acoustic signal levels that would otherwise be required absent the voltage biasing element 102. In the illustrated embodiment of FIG. 5, the DC bias element 102 biases the signal detector 100 to a level just below that necessary to generate the activation trigger signal. As will be described below, the DC voltage generated by the DC bias element 102 may be static, may be produced by expending some current from the energy storage device 80, or may be dynamically derived from the external activation signal.

In the illustrative embodiment of FIG. 5, the deactivation/activation switch component 86 is shown coupled between the signal detector 84 and a load (which represents the impedance of the control/processing circuitry 76), and includes three MOSFET transistors Q1-Q3, two resistors R1 and R2, and a switch S1. The transistor Q1 is a P-channel transistor and the transistors Q2 and Q3 are N-channel transistors. When the implantable device 66 is in the standby state, all of the transistors Q1-Q3 are turned off. To maintain this off-state, the gates of the transistors Q1-Q3 are biased by pull-down resistor R1 and pull-up resistor R2. The gate of the P-channel transistor Q1 is biased to the supply voltage $V_{cc}$, and the gates of the N-channel transistors Q2 and Q3 are biased to ground. During this quiescent stage, the switch S1 is closed and no current flows to the control/processing circuitry 76. Therefore, although an energy storage device is coupled to the supply voltage $V_{cc}$ and the ground is connected to the switch component 86, only a very small amount of current is drawn from the energy storage device.

When the acoustic transducer 82 detects an external acoustic activation signal (e.g., a signal having a particular frequency such as the transducer's resonant frequency), the acoustic transducer 82 generates an AC signal that is combined with the DC bias voltage to exceed the threshold voltage of the signal detector 84. As a result, an activation trigger signal (represented by a drop in voltage from $V_{cc}$ to a smaller value) is output by the signal detector 84. This drop in voltage switches-on the P-channel transistor Q1, which begins to conduct through the transistor Q1 and the pull-down resistor R1. As a result of the current flowing through transistor Q1, the voltage on the drain of the transistor Q1 and the gates of the transistors Q2 and Q3 increases from substantially zero to an amount sufficient to turn on transistors Q2 and Q3.

This increase in voltage switches-on the transistors Q2 and Q3. As a result, the transistor Q2 begins to conduct through resistor R2, and the transistor Q3 begins to conduct through the load, thereby conducting current to the control/processing circuitry 76 and activating the implantable device 66. As a result of the current flowing through the transistor Q2, the gate of the transistor Q1 is connected to ground through the transistor Q2, irrespective of whether or not signal detector 84 is currently outputting the activation trigger signal. At this stage, the transistors Q1-Q3 are latched to the conducting state even if the voltage generated by the acoustic transducer 82 is subsequently reduced to zero and the signal detector 84 ceases generating the activation trigger signal. Thus, current will continue to flow to the control/processing circuitry 76 until the switch S1 is opened.

In order to deactivate or open the switch component 86, the switch S1 must be opened (e.g., by the control/processor circuitry 76). If this occurs, the gate of the transistor Q1 increases to Vcc. The transistor Q1 then switches off, thereby switching off the transistors Q2 and Q3. At this state, current ceases flowing to the control/processing circuitry 76, thereby returning the implantable device 66 to its standby state even if the switch S1 is again closed. The switch component 86 will only return to its active state upon receiving a new acoustic activation signal from the acoustic transducer 82.

Other types of switch components can be used in some embodiments in addition to that shown in FIG. 5. For example, the switching operation may be performing using a complementary metal-oxide-semiconductor (CMOS) circuit such as a set-reset flip-flop, which may draw less current when switched-on, an electromechanical switch, or any other switch that can selectively allow/prevent the flow of current from the energy storage device 78 to the control/processing circuitry 76 in response to an activation trigger signal. Examples of other switching components that can be utilized include, but are not limited, to SR latches (e.g., cross-coupled NOR gates, cross-coupled NAND gates), D-latches, and flip-flops (e.g., master-slave flip-flops, JK flip flops).

Figure 6:
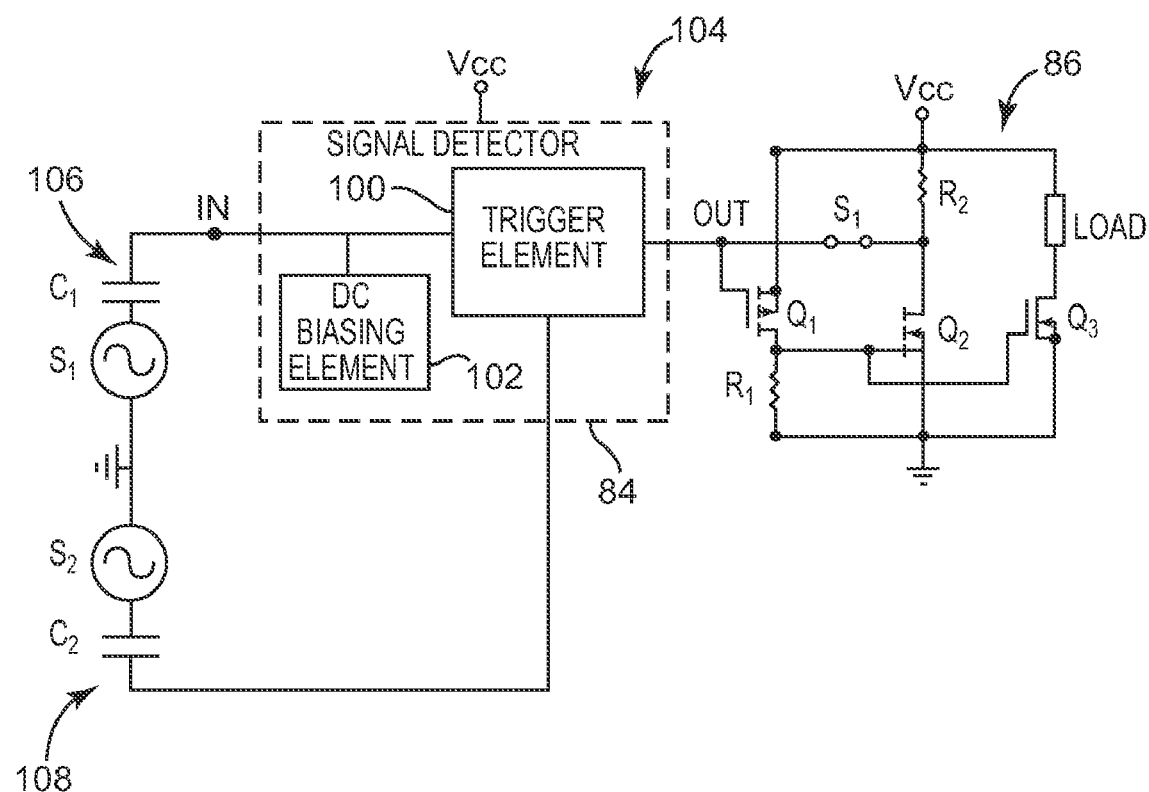
FIG. 6 is a circuit diagram of another embodiment of an acoustic switch that can be used in the implantable system of FIG. 4.

FIG. 6 is a circuit diagram showing another illustrative embodiment of an acoustic switch 104 that can be used in the implantable system of FIG. 4. The acoustic switch 104 is similar to the acoustic switch 80 illustrated in FIG. 4, with the exception that the signal detector 84 is coupled to two acoustic transducers 106,108 to further enhance the wake-up sensitivity of the implantable device 66. For example, if the trigger element 100 takes the form of a transistor, the first transducer 106 can be coupled to the gate or base of the transistor and the second transducer 108 can be coupled to the source or emitter of the transistor. In this manner, the gate-source voltage or the base-emitter voltage would be increased, thereby increasing the drain or collector pull-down voltage. The resulting voltage threshold required to generate the activation trigger signal would be approximately half that of the single transducer embodiment illustrated in FIG. 5. In some cases, this arrangement may avoid the enhanced parasitic effects that would be seen if the two transducers 106,108 were simply connected in series.

Although the transducer arrangement illustrated in FIG. 6 is shown in combination with the DC bias element 102, in other embodiments the transducer arrangement could be implemented without DC biasing the signal detector 84. Furthermore, in some embodiments more than two acoustic transducers are used to further reduce the voltage threshold required to generate the activation trigger signal. In some embodiments, for example, an array of transducer elements are used to reduce the voltage threshold.

The signal detector 84 and DC biasing element 102 can be implemented in any one of a variety of manners. In one embodiment illustrated in FIG. 7, for example, a signal detector 110 includes an N-channel transistor Q1 having a control gate g capacitively coupled to the input terminal IN, a drain d coupled to the supply voltage Vcc via a load resistor R1, and a source s coupled to ground. When the voltage at the input terminal IN does not exceed the voltage threshold of the transistor Q1 (i.e., the signal detector 110 does not detect a signal), no current flows through resistor R1 so that the voltage on the output terminal OUT is equal to Vcc. When the voltage at the input terminal IN does exceed the voltage threshold of the transistor Q1 (i.e., the signal detector 110 detects a signal), current flows through load resistor R1 so that the voltage at the output terminal OUT drops, thereby producing an activation trigger signal.

In some embodiments, the transistor Q1 is a Floating Gate MOSFET (FGFET), which comprises a standard MOSFET structure and an additional conducting plate fg (known as the floating gate) buried in the oxide underneath the control gate g. In this case, the standard MOSFET structure serves as the trigger element 100, and the floating gate fg serves as a DC biasing element 102. FGFETs are well known in the art, and are commonly used in components such as Electrically Erasable Programmable Read Only Memories (EEPROM's) and Flash memories. With respect to memories, FGFETs operate by utilizing the effect of the trapped charges on the voltage threshold of the resulting FET. In particular, the charge is transferred to or from the floating gate fg, resulting in a threshold change that can be detected by circuitry as a condition of a memory bit.

The control voltage of the transistor Q1 consists of the voltage on the control gate g (as in a standard MOSFET) plus the DC bias voltage resulting from any charge trapped in the floating gate fg. Thus, the positive charge stored on the floating gate fg adds to the AC voltage applied to the input terminal IN by the acoustic transducer 82 so that the transistor Q1 has a higher effective gate voltage. In the illustrated embodiment, the positive electrical charge is stored on the floating gate fg in a manner that shifts the threshold voltage of the transistor Q1 as far down as possible to minimize the AC voltage required at the input terminal IN for the signal detector 110 to produce the activation trigger signal while still ensuring an acceptably low rate of false activations. In other words, the transistor Q1 is biased near the threshold of conduction to maximize the activation sensitivity of the implantable device 66 even in the presence of process variations. The positive charge on the floating gate fg can be set during manufacture of the implantable device 66. Alternatively, or in addition, the charge may be transferred to the floating gate by on-board electronic circuits during the active state of the implantable device 66.

Figure 8:
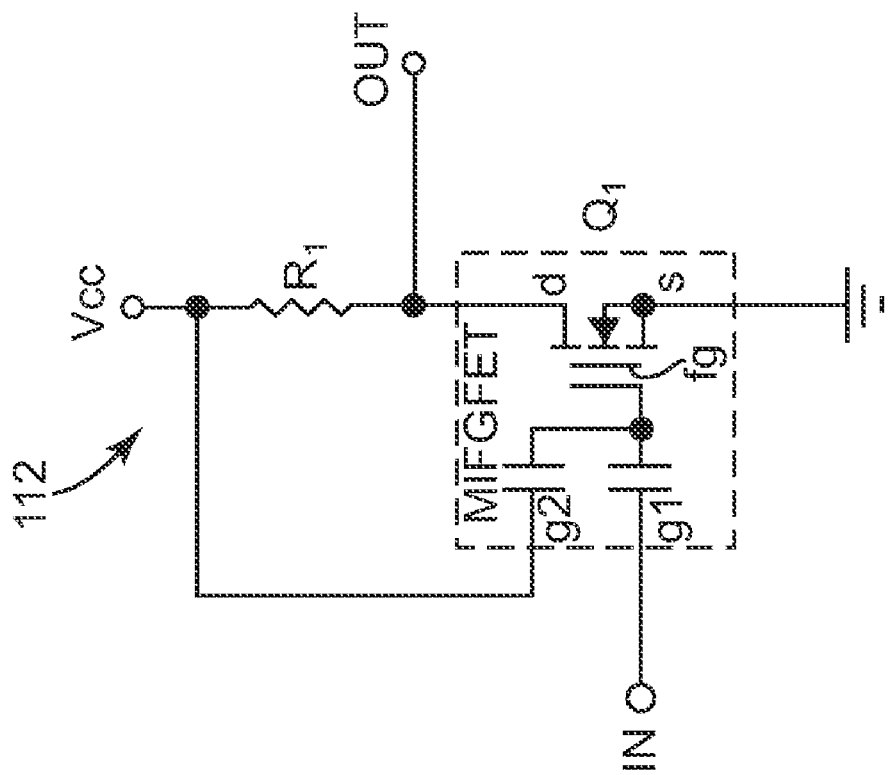
FIG. 8 is a circuit diagram showing another embodiment of a signal detector for use with the acoustic switches of FIGS. 5 and 6.

FIG. 8 is a circuit diagram showing another illustrative signal detector 112 for use with the acoustic switches of FIGS. 5 and 6. As shown in FIG. 8, the signal detector 112 is similar to the signal detector 110 of FIG. 7 with the exception that the signal detector 112 includes an N-channel transistor Q1 comprising a Multiple Input Floating Gate MOSFET (MIFGFET), which includes a standard MOSFET structure with a plurality of control gates g1, g2 deposited above a buried floating gate of the FGFET. Again, the standard MOSFET structure serves as the trigger element 100 and the floating gate fg serves as a DC biasing element 102. The control gates g1, g2 are capacitively coupled to the floating gate fg, with one control gate g1 coupled to the input terminal IN and the other control gate g2 coupled to the supply voltage Vcc.

Each control gate capacitance is proportional to the physical area of the overlap of the control gate g1,g2 over the floating gate fg. In the absence of a stored charge on the floating gate fg, the effective gate voltage is the weighted sum of the two control gate voltages with the weighting being given by the capacitance (i.e., by the ratio of the areas of the two control gates g1, g2). The control gate g2 coupled to the supply voltage Vcc supplies the charge to the floating gate fg, thereby obviating the need to inject charge through the isolation oxide that would otherwise be performed during a programming phase of the fabrication process. Since a potential is continually applied to the floating gate fg, the use of a MIFGFET is less sensitive to charge leakage, although the use of the single gate FGFET of FIG. 7 may be employed if the supply voltage $V_{cc}$ is not stable. Alternatively, the control gate g2 may supply a portion of the DC biasing with the remaining portion of the DC biasing being supplied by charge stored in the floating gate fg. This would be useful, for example, when the control gate g2 provides the bulk of the DC bias while the stored charge enables fine tuning during manufacture and/or operation of the implantable device 66.

Figure 7:
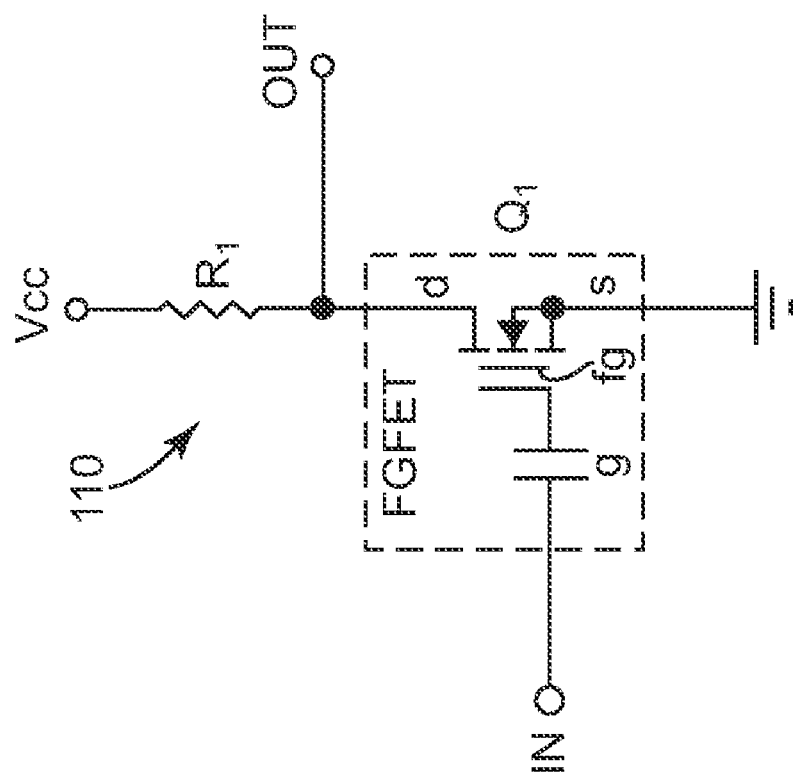
FIG. 7 is a circuit diagram showing an illustrative signal detector for use with the acoustic switches of FIG. 5 and 6.

In another embodiment, the transistor Q1 illustrated in FIG. 7 can take the form of a ferroelectric FET. The bias potential on a FET may be supplied by a permanent electric dipole present in ferroelectric materials. In this case, the FET comprises a Metal-Ferroelectric-Insulator-Semiconductor (MFIS) structure such as that described in Hiroshi Ishiwara, Current Status and Prospects of FET-Type Ferroelectric Memories, Journal of Semiconductor Technology and Science, Vol. 1, No. 1, March 2001, and in U.S. Pat. No. 6,960,801, entitled "High Density Single Transistor Ferroelectric Non-volatile Memory," which is expressly incorporated herein by reference in its entirety. As described therein, the usual FET gate oxide is replaced by a thin ferroelectric layer (which serves as the DC biasing element) comprising a material such as Lead Zirconate Titanate (PZT), Barium Titanate (BaTiO$_3$), or Strontium Bismuth Tantalite Oxide (SBT).

The voltage threshold of the ferroelectric FET can be raised or lowered by inducing a permanent polarization of the ferroelectric gate material. In this manner, similar to the transistors Q1 illustrated in FIGS. 7 and 8, the positive charge stored on the gate adds to the AC voltage applied to the input terminal IN by the acoustic transducer 82 so that the gate of the transistor Q1 sees a higher effective gate voltage, thereby minimizing the AC voltage required at the input terminal IN for the signal detector 84 to produce the activation trigger signal.

Figure 9:
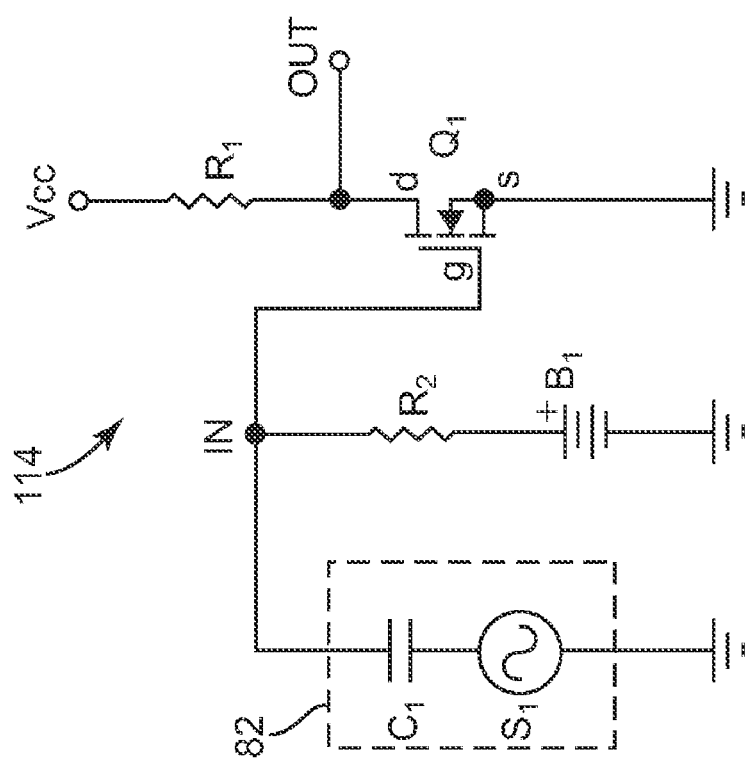
FIG. 9 is a circuit diagram showing another embodiment of a signal detector for use with the acoustic switches of FIGS. 5 and 6.

FIG. 9 is a circuit diagram showing another illustrative signal detector 114 for use with the acoustic switches of FIGS. 5 and 6. As shown in FIG. 9, the signal detector 114 is similar to the signal detector 110 illustrated in FIG. 7 with the exception that the N-channel transistor Q1 comprises a standard MOSFET that serves as the triggering element 100. Instead of a floating gate, the signal detector 114 includes a DC biasing element that biases the gate of the transistor Q1 by applying a DC charge on the intrinsic capacitance C1 of the acoustic transducer 82, which, as discussed above, can be modeled as a sinusoidal source S1 and a capacitor C1. Alternatively, a discrete capacitor (not shown) in series with the acoustic transducer 82 (or in the case of electromagnetic or magnetic communications means, the antenna) can be charged.

This DC voltage will not cause current to flow through the acoustic transducer 82 since there is no DC path to ground through the capacitor C1. The DC voltage applied to acoustic transducer 82 is typically at a level just under the voltage threshold of the transistor Q1. Thus, like the previous embodiments, the positive charge stored on the acoustic transducer 82 adds to the AC voltage applied to the input terminal IN by the acoustic transducer 82 so that the gate of the transistor Q1 has a higher effective gate voltage, thereby minimizing the AC voltage required at the input terminal IN for the signal detector 114 to produce the activation trigger signal.

In the embodiment of FIG. 9, the DC biasing element that applies the voltage to the acoustic transducer 82 comprises a built-in battery B1. The voltage of the battery B1 may be designed to the desired voltage by the appropriate selection of cathode and anode materials. For example, use of a gold cathode and nickel anode may result in a battery voltage of approximately 300 mV, which is an appropriate bias voltage for low-voltage FET's as well as for low current bipolar devices. Notably, there is no DC current path from the battery B1 to ground, and consequently no current is drawn from the battery B1. A resistor R2 is provided to decouple the low impedance battery B1 from the acoustic transducer 82 so that the time-varying electrical signal generated by the transducer 82 is not shorted to ground through the battery B1, and is thus applied to the gate of the transistor Q1. The only current extracted from the battery B1 results from the time-varying electrical signal itself, causing some current to flow through the resistor R1 during the generation of the time-varying electrical signal. However, this current leakage is negligible, and the lifetime of the battery B1 is thus limited only by its rate of self discharge.

Figure 10:
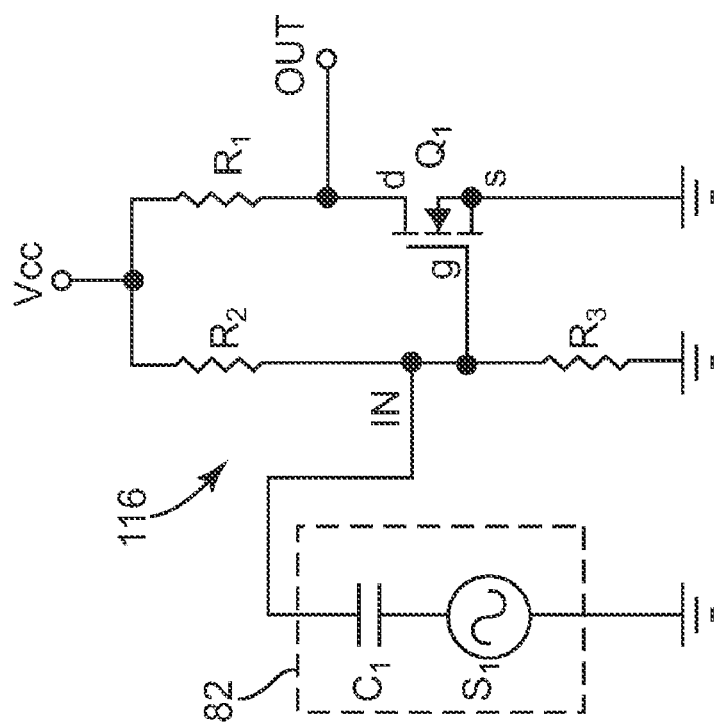
FIG. 10 is a circuit diagram showing another embodiment of a signal detector for use with the acoustic switches of FIGS. 5 and 6.

FIG. 10 is a circuit diagram showing another illustrative signal detector 116 for use with the acoustic switches of FIGS. 5 and 6. As shown in FIG. 10, the signal detector 116 is similar to the signal detector 114 illustrated in FIG. 9 with the exception that the DC bias potential applied to the intrinsic capacitance C1 of the acoustic transducer 82 (or alternatively, a discrete capacitor in series with the acoustic transducer 82) is derived from the energy storage device 78. In some embodiments, the DC biasing element comprises a voltage divider including a resistor R2 coupled between the supply voltage $V_{cc}$ and the gate of the transistor Q1 and a resistor R3 coupled between the gate of the transistor Q1 and ground, thereby providing a DC bias voltage across the transducer 82. In certain embodiments, the voltage divider is a resistor divider, which adds a DC bias equivalent to the signal based on the following formula:

$$Vbias = \frac{R_3}{R_2 + R_3} V_{CC}$$

The values of the resistors R2 and R3 are typically selected to be relatively high (e.g., in the 10's of mega-ohms or a few giga-ohms), so that negligible current flows across the voltage divider. The current through the voltage divider can also be made negligibly small since the DC impedance of the transducer 82 and the gate of the transistor Q1 tends to be quite large (e.g., in the teraohm range or larger). For example, currents in the range of about 20 pA-20 nA can be used in some embodiments, which is similar to typical semiconductor leakage currents that are too low to operate electronics but which are sufficient to charge the intrinsic capacitance C1 of the transducer 82 after sufficient period of time has elapsed.

There are a variety of additional methods of deriving a DC bias from the energy storage device 78 using negligible amounts of current. For example, the resistor R3 can be replaced by a transistor or diode, which can produce a voltage equal to the diode voltage just before conduction. This has the advantage of being relatively insensitive to the supply voltage Vcc. Similarly, resistor R3 may be replaced by a diode-connected MOSFET whose area has a well-defined relation to the area of MOSFET Q1 in the current mirror configuration. In this manner, the quiescent current flowing through R1 may be precisely controlled to be in a desired relation to the current through R2. This may achieve an optimal operating point for the circuit in which the quiescent current is minimized for the desired activation threshold. In other embodiments, the resistor R2 can be replaced by a very high impedance device such as a reverse biased leaky diode or a leaky transistor, or a MOSFET transistor with a very long channel. This may be useful in monolithic Very Large-Scale Integration (VLSI) implementations since very high resistor values are difficult to produce in silicon dies.

Figure 11:
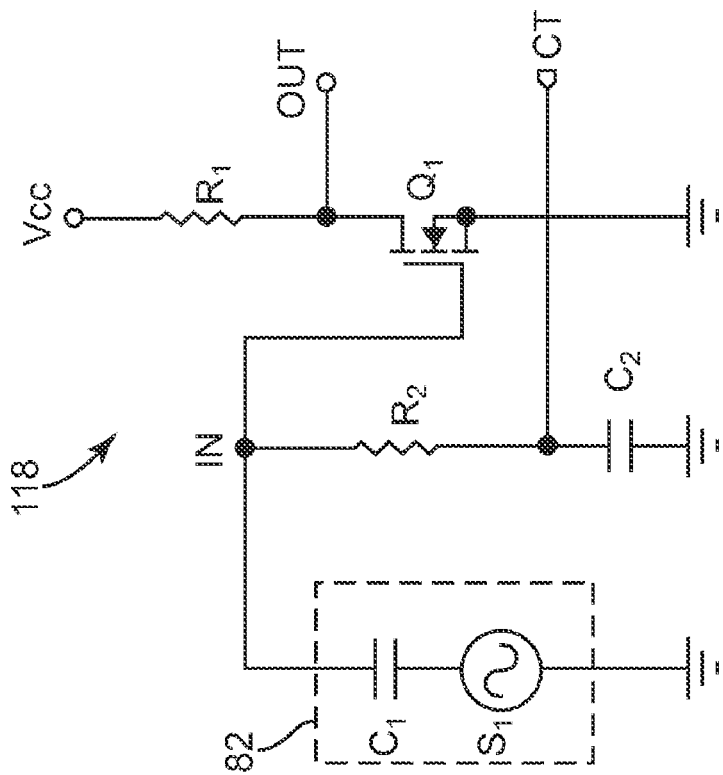
FIG. 11 is a circuit diagram showing another embodiment of a signal detector for use with the acoustic switches of FIGS. 5 and 6.

FIG. 11 is a circuit diagram showing another illustrative signal detector 118 for use with the acoustic switches of FIGS. 5 and 6. As shown in FIG. 11, the signal detector 118 is similar to the signal detector 114 illustrated in FIG. 9 with the exception that the DC bias potential is applied to the acoustic transducer 82 using a holding capacitor. In some embodiments, the DC biasing element comprises a capacitor C2 coupled to the gate of the transistor Q1 via the resistor R2. The capacitor C2 may be charged to the desired bias voltage via a charger terminal CT, thereby applying the voltage bias to the intrinsic capacitance C1 of the acoustic transducer 82 (or alternatively, a discrete capacitor in series with the acoustic transducer 82), when the implantable device 66 is in the active state. The capacitor C2 may be charged by any active circuit, including the control/processing circuitry 76. The voltage on the capacitor C2 is then retained after the implantable device 66 is placed in the standby state so that the signal detector 118 remains DC biased. Thus, the mean power consumption that occurs when the implantable device 66 is in the standby state is just the capacitor leakage, which can be made very small. Although the charge on the capacitor C2 may leak, potentially causing degradation to the wakeup sensitivity of the implantable device 66 over time, any leakage may not have an adverse effect if the implantable device 66 is activated periodically such as for hourly or daily operation.

Figure 12:
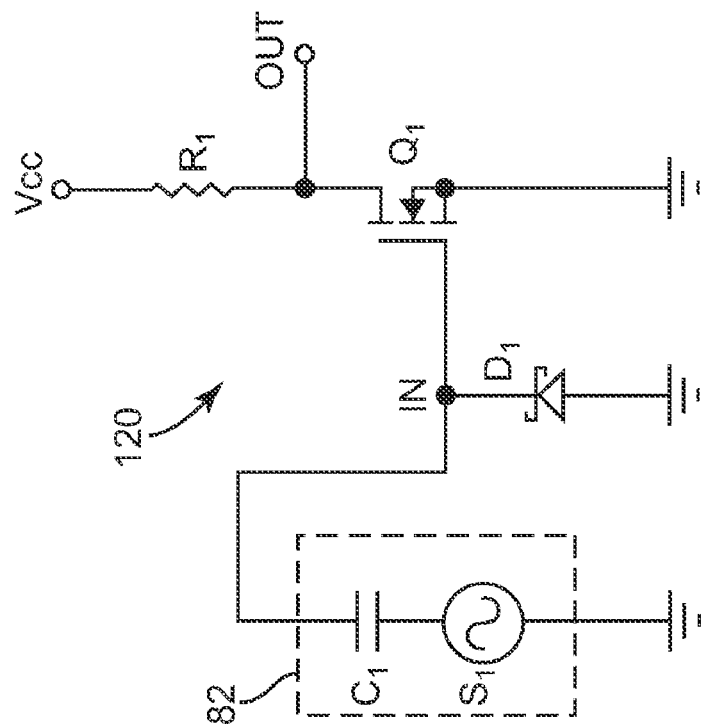
FIG. 12 is a circuit diagram showing another embodiment of a signal detector for use with the acoustic switches of FIGS. 5 and 6.

FIG. 12 is a circuit diagram showing another illustrative signal detector 120 for use with the acoustic switches of FIGS. 5 and 6. As shown in FIG. 12, the signal detector 120 is similar to the signal detector 114 illustrated in FIG. 9 with the exception that the DC bias potential is applied to the acoustic transducer 82 by rectifying the AC electrical signal generated by the acoustic transducer 82. In some embodiments, the DC biasing element comprises a Schottky diode D1 coupled between the gate of the transistor Q1 and ground. Schottky diodes are characterized by low forward voltage drops and fast switching times.

In use, the Schottky diode D1 shorts out the negative portion of the AC electrical signal, thereby causing current to flow into the intrinsic capacitance C1 of the acoustic transducer 82 to build up a positive DC potential on the acoustic transducer 82 (or alternatively, a discrete capacitor in series with the acoustic transducer 82). Alternatively, the circuit may be implemented in a flipped configuration with N-channel transistor Q1 replaced by a P-channel transistor whose source is coupled to $V_{cc}$ and whose drain is coupled via load resistor R1 to ground, and the Schottky diode D1 connected between the gate of transistor Q1 and $V_{cc}$. In such a configuration, the Schottky diode D1 shorts out the positive portion of the AC electrical signal, thereby causing current to flow into the intrinsic capacitance C1 of the acoustic transducer 82 to build up a negative DC potential relative to $V_{cc}$ on the acoustic transducer 82 (or alternatively, a discrete capacitor in series with the acoustic transducer 82). The signal detector would then be activated by the gate voltage of transistor Q1 dropping sufficiently below $V_{cc}$.

The threshold voltage of the Schottky diode D1 is lower than the voltage threshold of the transistor Q1 so that the charge can build up on the acoustic transducer 82 when the voltage level of the electrical signal is less than the voltage threshold of the transistor Q1. In the case of a Schottky diode, the diode action results from a metal-semiconductor junction rather than a semiconductor-semiconductor junction such as in bipolar transistors so that very low voltage thresholds may be achieved for low current. In another embodiment, the diode D1 comprises a low bandgap semiconducting material such as germanium.

Figure 13:
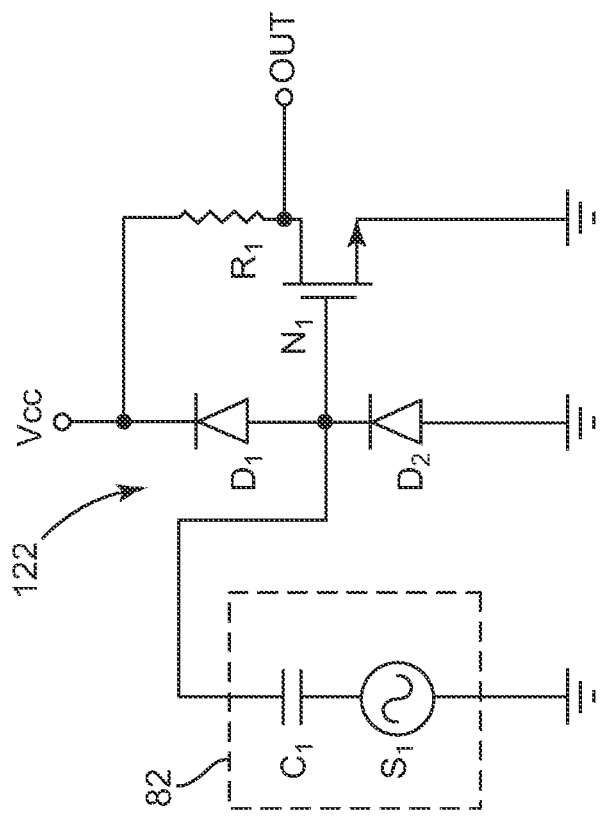
FIG. 13 is a circuit diagram showing another embodiment of a signal detector for use with the acoustic switches of FIGS. 5 and 6.

FIG. 13 is a circuit diagram showing another illustrative signal detector 122 for use with the acoustic switches of FIGS. 5 and 6. As shown in FIG. 13, the signal detector 122 includes a low threshold NMOS transistor N1 (or alternatively a low threshold PMOS transistor in reverse) coupled to several reverse-biased diodes D1,D2, which function similar to the resistor divider circuit described above with respect to FIG. 10, but which require less current to provide the DC biasing and produce less parasitic capacitance in the signal path between the acoustic transducer 82 and the gate of the transistor N1. This is useful, for example, when the intrinsic capacitance C1 of the acoustic transducer 82 is small since parasitic capacitance in the signal path can reduce the level of the signal reaching the gate of the transistor N1.

As with a resistor divider circuit, each of the diodes D1,D2 can be configured so that a desired voltage bias is generated to minimize the AC voltage required at the transistor N1 to produce the activation trigger signal. A first reverse-biased diode D1 is connected to $V_{cc}$ and to the gate of the transistor N1. A second reverse-biased diode D2, in turn, is connected to the gate of the transistor N1 and ground. In some embodiments, each of the diodes D1,D2 comprise Schottky diodes. In other embodiments, other types of diodes can be implemented.

In certain embodiments, each of the diodes D1,D2 can be replaced by multiple diodes arranged in cascading fashion in order to further reduce the AC voltage required at the transistor N1 to produce the activation trigger signal. In some embodiments, for example, diode D1 shown in FIG. 13 can be replaced with multiple forward-biased diodes each connected in series with each other. In similar fashion, the diode D2 shown in FIG. 13 can be replaced with multiple forward-biased diodes each connected in series with each other.

Figure 14:
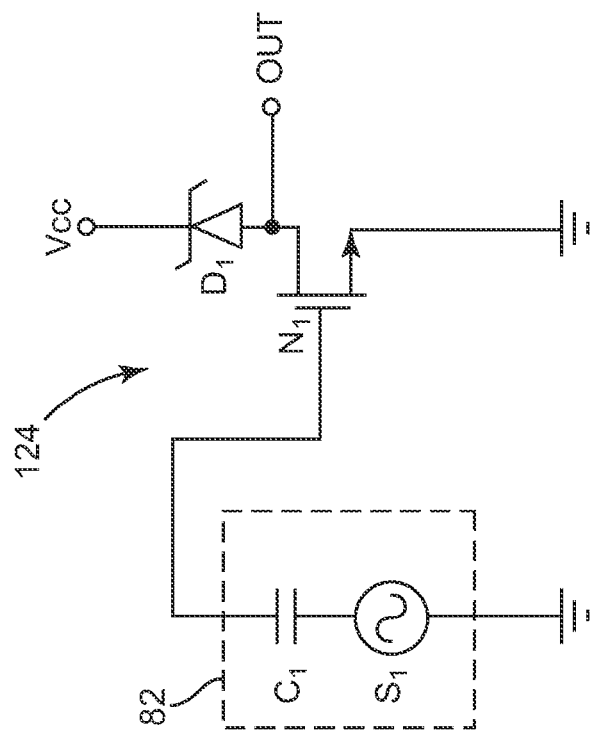
FIG. 14 is a circuit diagram showing another embodiment of a signal detector for use with the acoustic switches of FIGS. 5 and 6.

FIG. 14 is a circuit diagram showing another illustrative signal detector 124 for use with the acoustic switches of FIGS. 5 and 6. As shown in FIG. 14, the signal detector 124 includes an NMOS transistor N1 coupled to a reverse-biased diode D1. The diode D1 can be configured to function similar to the resistor R1 used in the embodiment of FIG. 7 by pulling-up the voltage at the collector for the transistor N1, which decreases the activation threshold required to activate the transistor N1 similar to a resistor but without significantly increasing parasitic capacitance, An example diode D1 that can be used in some embodiments is a "leaky" diode such as a Schottky diode, which increases the resistance for the pull-up without significantly increasing the parasitic capacitance on the drain of the transistor N1.

Figure 15:
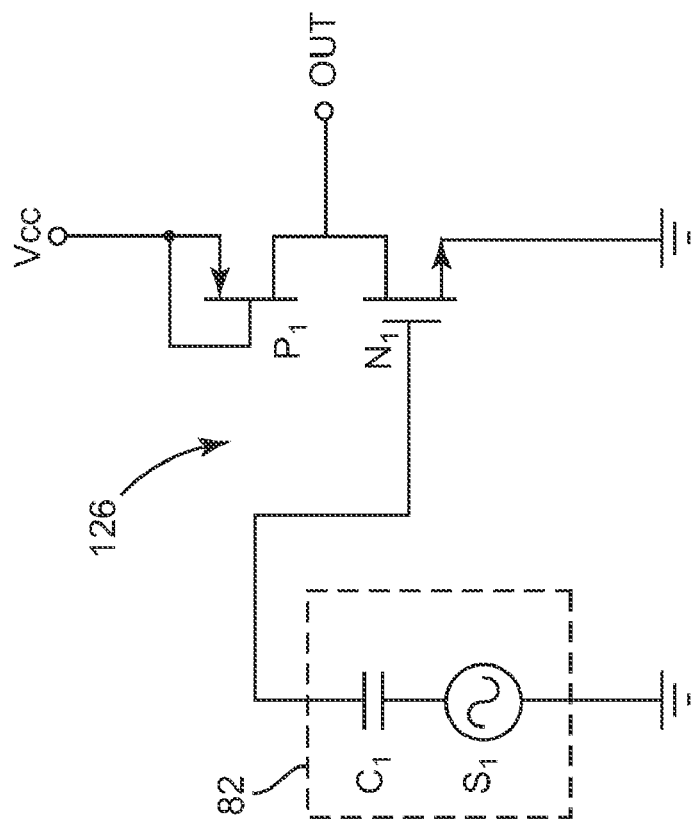
FIG. 15 is a circuit diagram showing another embodiment of a signal detector for use with the acoustic switches of FIGS. 5 and 6.

FIG. 15 is a circuit diagram showing another illustrative signal detector 126 for use with the acoustic switches of FIGS. 5 and 6. As shown in FIG. 15, the signal detector 126 is similar to the signal detector 124 illustrated in FIG. 14 with the exception that a diode-connected, low-threshold PMOS transistor P1 is used as a "leaky" device instead of a diode. In use, the PMOS transistor P1 functions by pulling-up the voltage at the drain of the transistor N1, thus reducing the threshold voltage required to activate the NMOS transistor N1. The diode-connected PMOS transistor P1 will generally have a much higher resistance than a resistor connected to $V_{cc}$.

Figure 16:
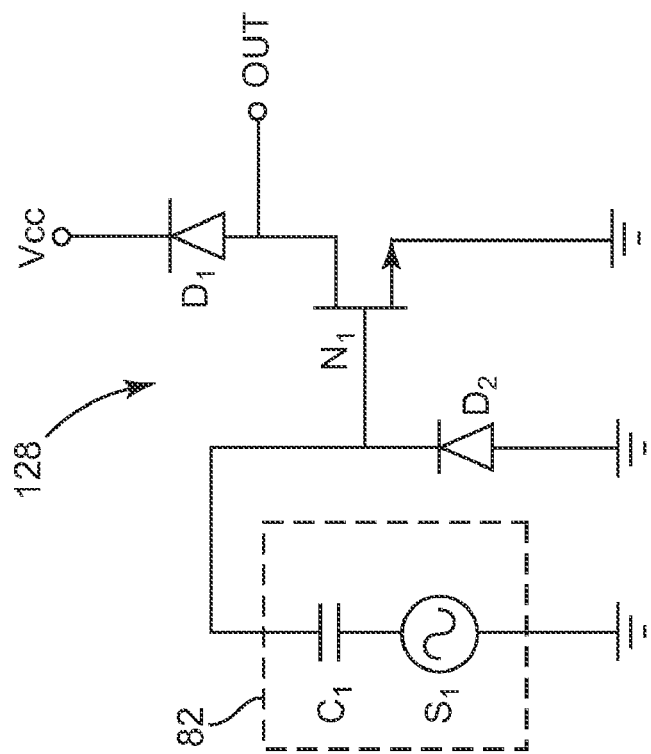
FIG. 16 is a circuit diagram showing another embodiment of a signal detector for use with the acoustic switches of FIGS. 5 and 6.

Many of the features of the illustrative signal detection circuits discussed herein can be combined together to form variations of the signal detection circuits useful for reducing the threshold voltage required to activate the acoustic switch. In one illustrative signal detector 128 depicted in FIG. 16, for example, the level-shifting diode provided in the embodiment of FIG. 12 is combined with a pull-up device such as the diode provided in the embodiment of FIG. 14, forming a signal detector 128 exhibiting features common to both embodiments. Other circuit variations are also contemplated for use with either a single acoustic transducer, as shown, for example, in FIG. 5, or multiple acoustic transducers, as shown, for example, in FIG. 6.

Figure 17:
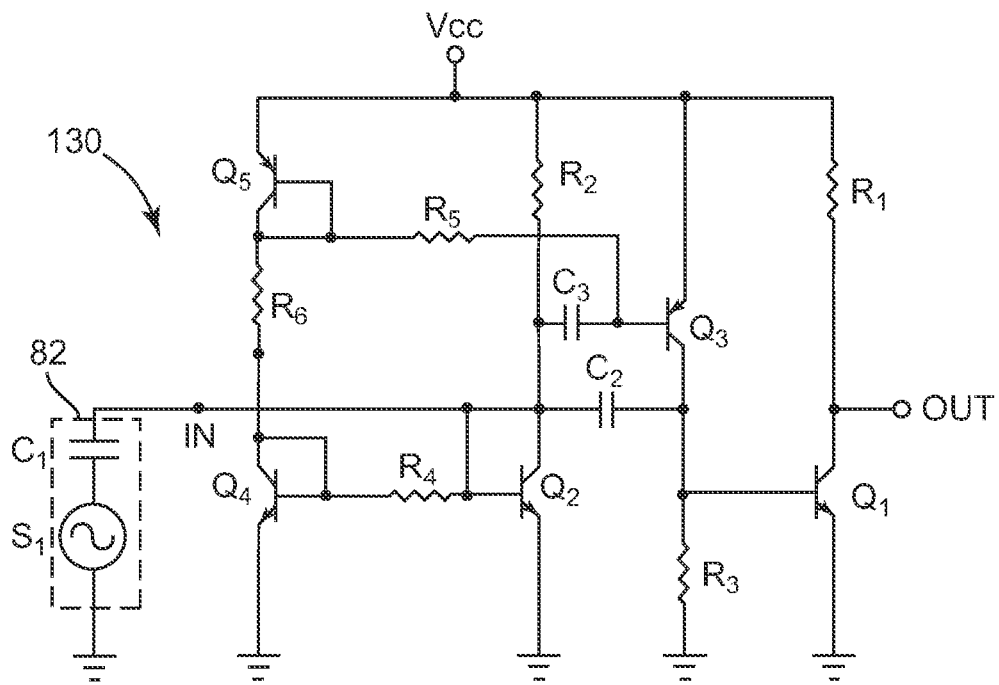
FIG. 17 is a circuit diagram showing another embodiment of a signal detector for use with the acoustic switches of FIGS. 5 and 6.

FIG. 17 is a circuit diagram showing another illustrative signal detector 130 for use with the acoustic switches of FIGS. 5 and 6. In the illustrative embodiment of FIG. 17, the signal detector 130 applies a DC bias voltage to the input terminal IN and further applies positive feedback to raise the DC bias voltage at the input terminal IN to a level that produces an activation trigger signal. In this embodiment, the signal detector 130 comprises a bipolar transistor Q1 and a positive feedback circuit comprised of transistors Q2, resistors R2, R3 and coupling capacitors C2, C3. Alternatively, in other embodiments MOSFET transistors may be used. The transistor Q1 has a base coupled to the output of the positive feedback circuit at the collector of Q3, a collector coupled to the supply voltage Vcc via a load resistor R1, and an emitter coupled to ground. When the voltage at the output of the positive feedback circuit does not exceed the voltage threshold of the transistor Q1 (i.e., the signal detector 30 does not detect a signal), no current flows through resistor R1 so that the voltage on the output terminal OUT is equal to Vcc. When the voltage at the output of the positive feedback circuit exceeds the voltage threshold of the transistor Q1 (i.e., the signal detector detects a signal), current flows through load resistor R1 so that the voltage at the output terminal OUT drops, thereby producing an activation trigger signal.

The signal detector 130 comprises a two-stage DC bias circuit that provides positive feedback that charges the capacitor C1 of the acoustic transducer 82 (or alternatively, a discrete capacitor in series with the acoustic transducer 82). In some embodiments, the signal detector 130 comprises a first stage bipolar transistor Q2 and a second stage bipolar transistor Q3 with the base of the first stage transistor Q2 coupled to the emitter of the second stage transistor Q3 via an AC coupling capacitor C2, and the base of the second stage transistor Q3 coupled to the collector of the first transistor Q2 via the AC coupling capacitor C3. The collector of the first stage transistor Q2 is coupled to the supply voltage Vcc via a resistor R2, and the collector of the second stage transistor Q3 is coupled to ground via a resistor R3. The base of the first stage transistor Q2 is also coupled to the input terminal IN.

In the illustrated embodiment, the bases of the transistors Q2 and Q3 are biased using current mirrors to program the nonlinear gain of the signal detector 130. In some embodiments the signal detector 130 includes a bipolar transistor Q4 with its emitter coupled to ground and its collector and base coupled to the base of the first stage transistor Q2 via a resistor R4 that isolates the AC signal from the DC bias, and a bipolar transistor Q5 with its collector coupled to the supply voltage $V_{cc}$ and its emitter and base coupled to the base of the second stage transistor Q3 via a resistor R5 that isolates the AC signal from the DC bias. The collector of the transistor Q4 is coupled to the emitter of the transistor Q5 via a current programming resistor R6, which can be selected to set the bias current flowing through the collectors of transistors Q4 and Q5, and thus also through the collectors of transistors Q2 and Q3. The bias voltage appears as a DC bias on the intrinsic capacitance C1 of the acoustic transducer 82 (or alternatively a discrete capacitor in series with the acoustic transducer 82). There are many other possible ways to bias the transistors Q2 and Q3. In some embodiments, for example, the transistors Q4, Q5 and resistor R6 can be replaced with other current source circuits known in the art.

The current mirrors are used to hold the signal detector 130 just under its critical gain, which is the gain that causes the circuit to start oscillating. In particular, the bias voltage applied to the transistors Q2, Q3 via the current mirrors is increased to maximize the gain and sensitivity of the signal detector 130 without causing the signal detector 130 to oscillate. In this state, the signal detector 130 is static and draws only the minimal current required for the DC biasing of the acoustic transducer 82. The addition of a small AC voltage coming from the acoustic transducer 82 to the quiescent current momentarily pushes the signal detector 130 above its critical point, resulting in a large response, and in particular, the generation of an activation trigger signal at the output terminal OUT.

In particular, when the acoustic transducer 82 generates the AC electrical signal in response to an acoustic activation signal, the base voltage of the first-stage transistor Q2 increases, which increases the collector current of the transistor Q2, thereby increasing the voltage drop across the collector resistor R2 and decreasing the collector voltage of the transistor Q2. As a result, the base voltage of the second-stage transistor Q3 decreases, which increases the collector current of the transistor Q3, thereby increasing the voltage drop across the collector resistor R3 and increasing the collector voltage of the transistor Q3. The increase in the collector voltage of the transistor Q3, in turn, injects current into the input terminal IN via the coupling capacitor C2, which charges the intrinsic capacitance C1 of the acoustic transducer 82 (or a discrete capacitor in series with the acoustic transducer 82), gradually increasing the DC bias at the input terminal IN, and further the collector currents of Q2 and Q3. Eventually, the collector current of Q3 increases to a level at which the voltage across collector resistor R3 is high enough to cause the transistor Q1 to generate the activation trigger signal.

Figure 18:
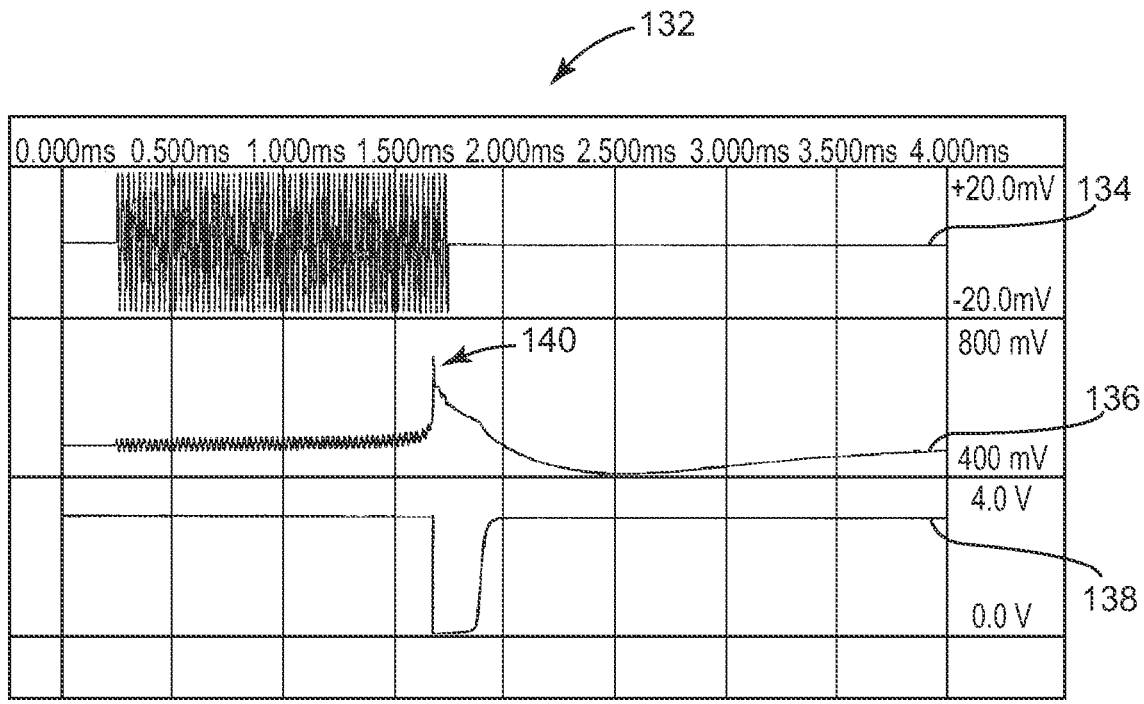
FIG. 18 is a diagram illustrating signal waveforms at various points within the signal detector of FIG. 17.

FIG. 18 is a diagram 132 showing several simulation waveforms 134,136,138 at various points within the signal detector 130 of FIG. 17. In this simulation, the resistors R1-R6 for the signal detector 130 were selected to be 1 MOhm, 100 MOhm, 100 MOhm, 20 MOhm, 100 MOhm, and 1 GOhm, the capacitors C1-C3 were selected to be 5 pF, 5 pF, and 22 pF, the supply voltage $V_{cc}$ was selected to be 3V, and the amplitude and frequency of the AC activation signal were selected to be 19 mV and 40 kHz, respectively. The bias current generated by each current mirror was approximately 1.3 nA, resulting in a total quiescent current consumption for the signal detector 130 of 3.4 nA.

As shown in FIG. 18, the top waveform 134 shows the input AC signal generated by the acoustic transducer 82, the middle waveform 136 shows the resulting signal at the input terminal IN, and the bottom waveform 138 shows the signal at the output terminal OUT. As can be appreciated, the input AC signal is superimposed on the DC bias signal to create the resultant signal (middle waveform 136) at the input terminal IN, with the resulting signal gradually increasing over time due to the DC bias signal increasing in response to the positive feedback. At a certain point in time, the signal detector 130 reaches a critical point 140 where the signal at the input terminal IN rises rapidly due to the runaway positive feedback, thereby causing the transistor Q1 to generate the activation trigger signal (bottom waveform 138) at the output terminal OUT.

Figure 19:
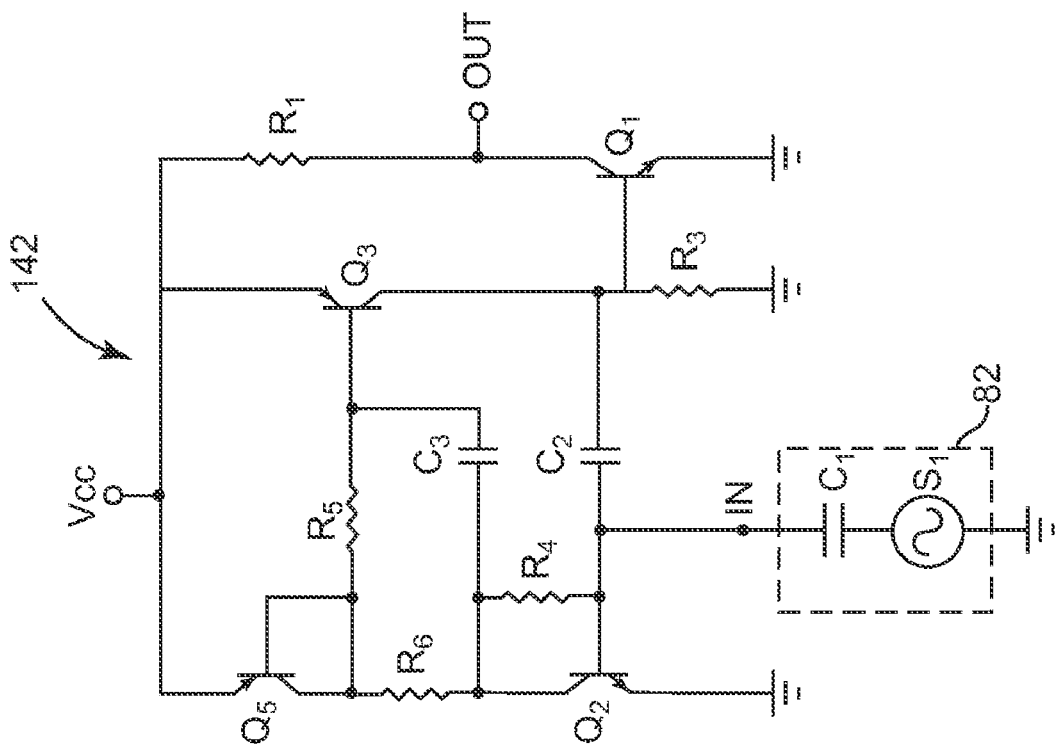
FIG. 19 is a circuit diagram showing another embodiment of a signal detector for use with the acoustic switches of FIGS. 5 and 6.

FIG. 19 is a circuit diagram showing another illustrative signal detector 142 for use with the acoustic switches of FIGS. 5 and 6. As shown in FIG. 19, the signal detector 142 is similar to the signal detector 130 illustrated in FIG. 17 with the exception that the current consumption is reduced by uniting the current programming branch with the first stage transistor. In particular, the current mirror transistor Q4 has been eliminated and, therefore, the transistor Q5 and resistor R6 programs the nonlinear gain of the signal detector 142 and biases the bases of the transistors Q2 and Q3.

As with the signal detector 130 described above, when the acoustic transducer 82 generates the AC electrical signal in response to an acoustic activation signal, the base voltage of the first-stage transistor Q2 increases, which increases the collector current of the transistor Q2, thereby increasing the voltage drop across the resistor R6 and decreasing the collector voltage of the transistor Q2. As a result, the base voltage of the second-stage transistor Q3 decreases, which increases the collector current of the transistor Q3, thereby increasing the voltage drop across the collector resistor R3 and increasing the collector voltage of the transistor Q3. The increase in the collector voltage of the transistor Q3, in turn, injects current into the input terminal IN via the coupling capacitor C2, which charges the intrinsic capacitance C1 of the acoustic transducer 82 (or a discrete capacitor in series with the acoustic transducer 82), gradually increasing the DC bias at the input terminal IN, and with it the collector current of Q3. Eventually, the collector current of Q3 increases to a level at which the voltage across collector resistor R3 is high enough to cause transistor Q1 to generate the activation trigger signal.

Figure 20:
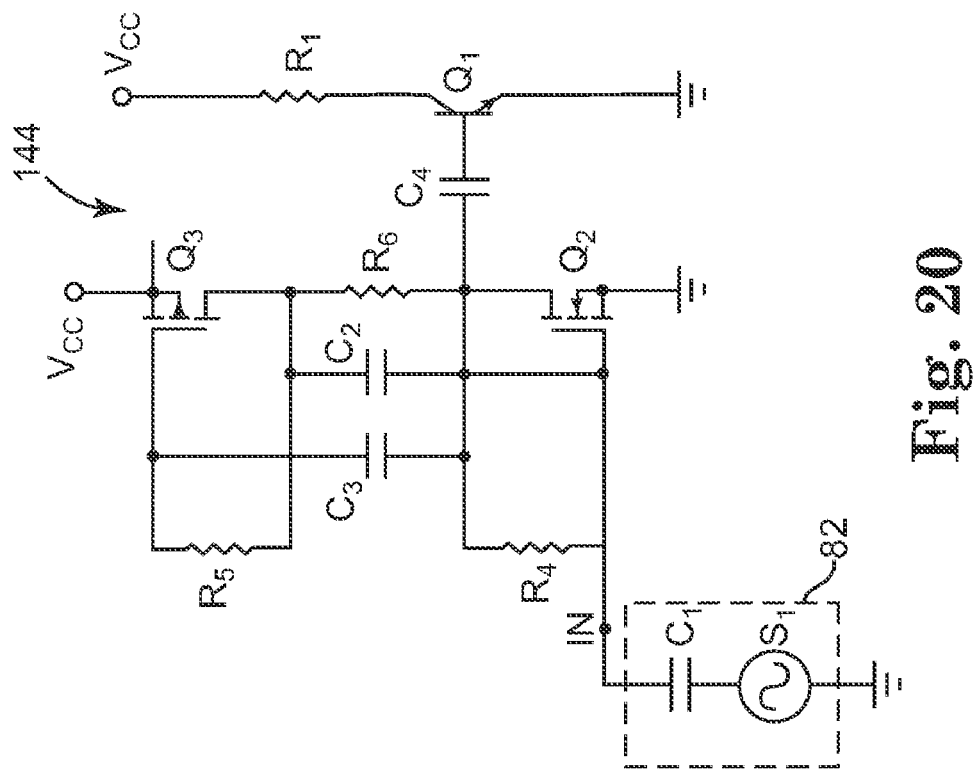
FIG. 20 is a circuit diagram showing another embodiment of a signal detector for use with the acoustic switches of FIGS. 5 and 6.

FIG. 20 is a circuit diagram showing another illustrative signal detector for use with the acoustic switches of FIGS. 5 and 6. As shown in FIG. 20, the signal detector 144 is similar to the signal detector 142 illustrated in FIG. 19 with the exception that the current consumption is further reduced by joining all of the detector functionality into a single current carrying-branch. In particular, the remaining current mirror transistor Q5 has been eliminated. Thus, in this case, the resistor R6 programs the nonlinear gain of the signal detector 144 and biases the bases of the transistors Q2 and Q3. As also shown in FIG. 20, and in some embodiments, the transistors Q2, Q3 can include MOSFET's rather than bipolar transistors, although bipolar transistors may also be used in other embodiments. The transistor Q1 may also take the form of a MOSFET or a bipolar transistor.

As with the signal detector 130 described above, when the acoustic transducer 82 generates the AC electrical signal in response to an acoustic activation signal, the gate voltage of first-stage transistor Q2 increases, which increases the drain current of the transistor Q2, thereby decreasing the drain voltage of the transistor Q2. As a result, the gate voltage of the second-stage transistor Q3 decreases, which increases the drain voltage of the transistor Q3. The charge for the voltage changes drawn from the coupling capacitors C2, C3 rather than from collector or drain load resistors since the impedance of the capacitors C2, C3 is lower than the impedance of the (typically very large) current setting resistor R6. The increase in the drain voltage of the transistor Q3, in turn, injects current into the input terminal IN via the coupling capacitor C2, which charges the intrinsic capacitance C1 of the acoustic transducer 82 (or a discrete capacitor in series with the acoustic transducer 82), gradually increasing the DC bias at the input terminal IN, and eventually causing the transistor Q1 to generate the activation trigger signal. Notably, the transistor Q1 in this embodiment cannot be connected directly to the drain of the transistor Q3 since the quiescent value of the drain voltage of the transistor Q3 is equal to Vcc minus the threshold of the transistor Q3, which would typically be above the threshold voltage of the transistor Q1. Instead, in the present embodiment the base of the transistor Q1 is AC coupled to the drain of the transistor Q3 via a capacitor C4 to ensure that the transistor Q1 is triggered not by the DC voltage of the drain of the transistor Q3, but instead only by the voltage upswing caused by the received signal. For a MOSFET, the voltage upswing is equal to the threshold voltage of the transistor Q3, which would typically be higher than the threshold voltage of the transistor Q1 when implemented as a bipolar transistor.

It should be noted that all of the embodiments depicted in FIGS. 7-17 and 19-20 may have their sensitivity increased in the manner outlined in FIG. 6. That is, in all of these cases one may connect two transducers to the detectors to approximately double their sensitivity, with a first transducer connected to the gate or base of the appropriate transistor, as depicted in the figures, and a second transducer connected between the source or emitter of the input transistor and ground. As a result, the gate-source or base-emitter voltage swing in response to a given acoustic excitation is increased by about a factor of two, thus enhancing the sensitivity of the signal detection circuit. In the case of MOSFET transistors, the effect is enhanced due to the body effect, which causes the transistor threshold to decrease as its source potential is lowered.

Some of the signal detectors described herein may be sensitive to unintentional excitations such as shocks, vibrations, or noises, some of which may be generated by the body of the patient itself or by other implanted medical devices such as mechanical heart valves or implantable pumps. In addition, the sensitivity and stability of some of the signal detectors may depend on small variations between components or on environmental factors such as temperature changes and aging. For example, the positive feedback signal detectors 130,142,144 may show good stability and sensitivity at a specific temperature, but may start to undesirably oscillate at a different temperature. In another example, there may be a significant spread in component values between different manufacturing batches, which complicates the manufacturing process. An additional factor affecting stability and sensitivity could be variations in battery voltage Vcc resulting from depletion of the battery.

As a result of the foregoing, the acoustic switches in which these signal detectors are incorporated may be susceptible to false activations, which can shorten the life of the battery. Differing environmental acoustic conditions can also cause false activations. For example, the acoustic and other environmental conditions during storage and transportation may cause numerous false activations. In another example, an implantable device may be present in a patient who is about to undergo a medical procedure such as surgery, which may cause false implant activations.

To reduce false positives (either false activations or deactivations), the implantable device 66 can be configured in some embodiments to be only fully activated upon receipt of an activation signal followed by a verification signal. Use of a verification signal may be especially useful when selecting specific implantable devices or a group of implantable devices using an activation signal, and then using a different verification signal to fully activate the implantable devices. In addition to an activation signal, the implantable device 66 can be configured to be deactivated (i.e., placed in the standby state) in response to a deactivation acoustic signal (which may be the same or different from the activation signal). For example, once the implantable device 66 is activated, the acoustic switch 80 may remain closed indefinitely (e.g., until the energy storage device 78 is depleted or until a deactivation signal is received by the acoustic switch 80). Alternatively, the acoustic switch 80 may include a timer (not shown) so that the switch 80 remains closed only for a predetermined time, whereupon the switch 80 automatically opens to return the implantable device 66 to its standby state.

Figure 21:
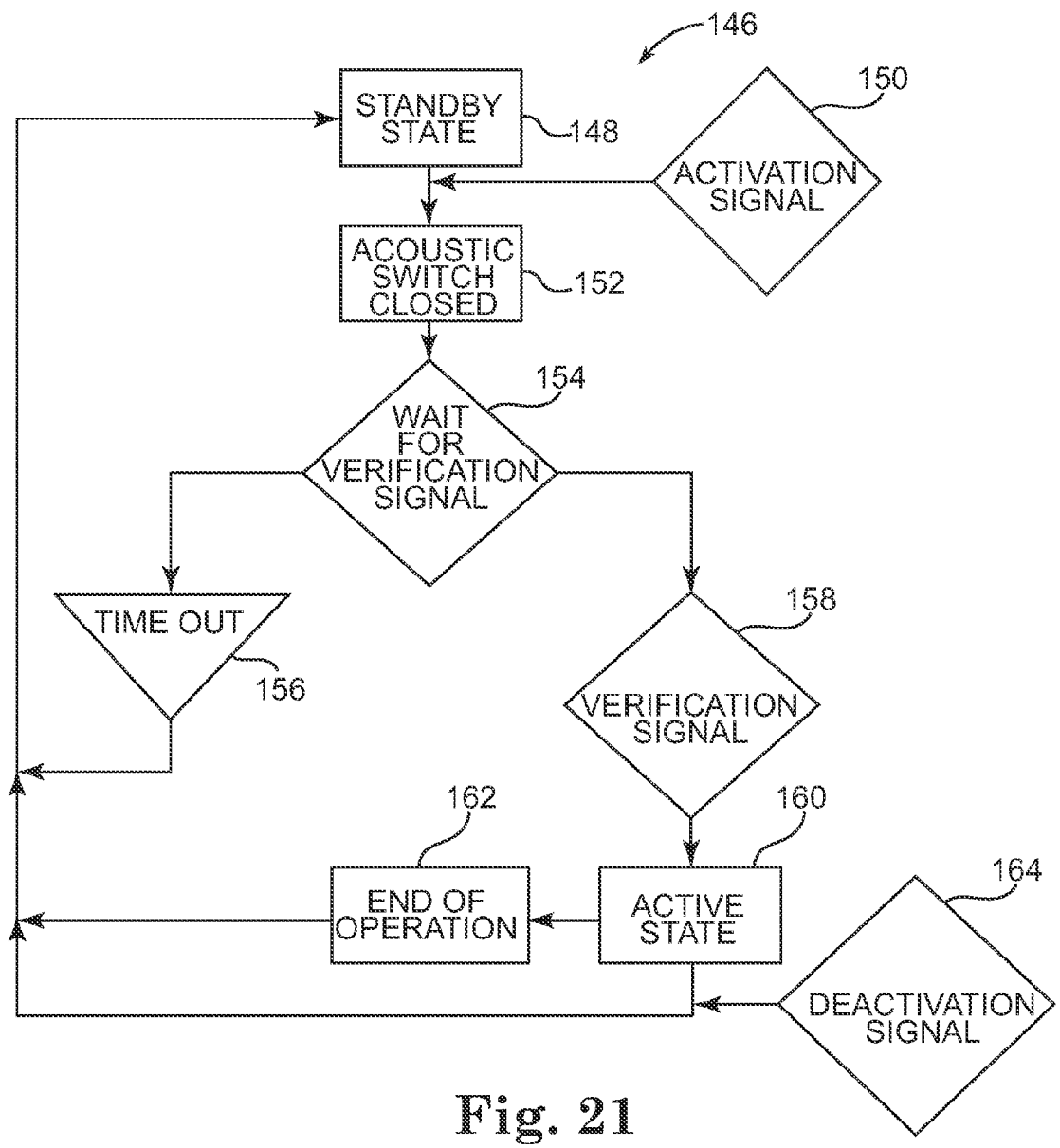
FIG. 21 is a flow diagram showing an illustrative method of activating an implantable device using an activation signal and a verification signal.

FIG. 21 is a flow diagram showing an illustrative method 146 of activating an implantable device using an activation signal and a verification signal. First, the implantable device 66, while in its standby state (block 148), receives an activation signal (block 150), after which the acoustic switch 80 is closed to activate a minimal portion of the control/processing circuitry 76 (block 152). The implantable device 66 then waits for a verification signal (block 154). If no verification signal is received by the implantable device 66 within a predetermined period of time (block 156), the control/processing circuitry 76 times out and the acoustic switch 80 is opened to return the implantable device 66 to its standby state (block 148). If a verification signal is received by the implantable device 66 within the predetermined period of time (block 158), the implantable device 66 is fully activated (block 160). When the medical function has been completed (block 162) or a deactivation signal has been received by the implantable device 66 (block 164), the acoustic switch 80 is opened to return the implantable device 66 to its standby state (block 148).

To further combat conditions that may cause false implant activations, the control/processing circuitry 76 illustrated in FIG. 4 may dynamically adjust the specific voltage threshold at which the AC electrical signal generated by the acoustic transducer 82 causes the signal detector 84 to generate the activation trigger signal by adjusting the DC biasing of the signal detector 84.

Figure 22:
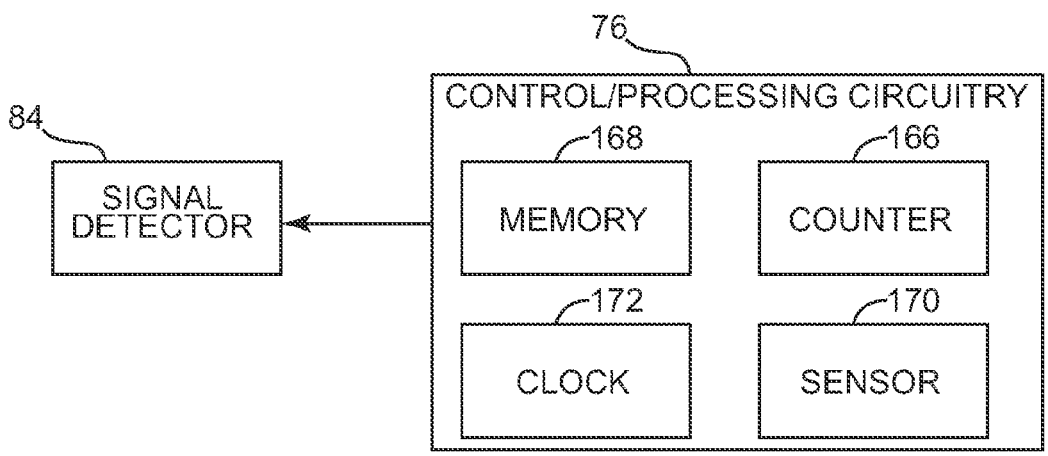
FIG. 22 is a block diagram showing control/processing circuitry for use with the system of FIG. 4.

In one embodiment, the control/processing circuitry 76 accomplishes this based on the occurrence of false activations. In some embodiments, the control/processing circuitry 76 includes means for detecting and counting false activations. For example, as discussed previously, the implantable device 66 may receive a verification signal in addition to an activation or wake-up signal. Thus, the control/processing circuitry 76, while the implantable device 66 has been activated by activation signal or inadvertent noise, may identify false activations by analyzing the received verification signals or lack thereof. These false activations can be counted and stored in a counter 166 or non-volatile memory 168 within the control/processing circuitry 76, as shown, for example, in FIG. 22. Once a certain number of false activations has been exceeded, either as an absolute number or in a predetermined period of time, the control/processing circuitry 76 may respond by raising the AC voltage threshold by adjusting the DC biasing of the signal detector 84 during the active state of the implantable device 66. The threshold may be reset automatically to its more sensitive level by the implantable device 66, for example, after every successful activation and verification session, or upon a command received from an external device.

In another embodiment, the control/processing circuitry 76 may indirectly estimate the probability of a false activation. For example, in some embodiments the control/processing circuit 76 can include a sensor 170 for sensing environmental conditions such as acoustic ambient noise levels (the noise source may be internal or external to the patient's body), temperature, acceleration, and the like. The sensor 170 may be a dedicated sensor, the biosensor 90, or even the acoustic transducer 82. Based on the output of the sensor 170, the control/processing circuitry 76 may then adjust the AC voltage threshold by adjusting the DC biasing of the signal detector 84 during the active state of the implantable device 66. For example, the AC voltage threshold may be adjusted according to the sensed temperature to conform to the expected temperature dependence of the signal detector 84. As another example, the AC voltage threshold may be increased in the presence of high ambient noise.

Many of the signal detectors discussed above conveniently allow the control/processing circuitry 76 to electronically control the AC voltage threshold. For example, the AC voltage threshold of the signal detector 110 illustrated in FIG. 7 can be adjusted by modifying the charge on the floating gate fg. This can be accomplished, for example, using a programming circuit such as that described in U.S. Pat. No. 6,970,037, entitled "Programmable Analog Bias Circuits Using Floating-Gate CMOS Technology," which is expressly incorporated herein by reference in its entirety. The AC voltage threshold of the signal detector 112 illustrated in FIG. 8 can be adjusted by switching between different gates and gate capacitances. For example, a bank of control gates g can be provided, any number of which can be connected in parallel to provide a given capacitance. The AC voltage threshold of the signal detector that uses a ferroelectric FET can be adjusted by varying the degree of polarization of the ferro-electric layer. The AC voltage threshold of the signal detector 116 illustrated in FIG. 10 can be adjusted by changing the values of one or both of the resistors of the voltage divider. This can be accomplished by using a digital variable resistor, e.g., one comprising a binary resistor series ladder and transistors that can short any desired resistor. A binary "word" on the transistor gates may give the corresponding ladder resistance without expending current. The AC voltage threshold of the signal detector 118 illustrated in FIG. 11 can be adjusted by varying the charge on the holding capacitor C2. The AC voltage threshold of the signal detectors 130, 142,144 illustrated in FIGS. 17, 19, and 20 can be adjusted by varying the bias current, the value of a component (resistor or capacitor), or the gain of the circuit. It can be appreciated that many other methods may be employed for varying the AC voltage threshold of the signal detectors described above.

Figure 23:
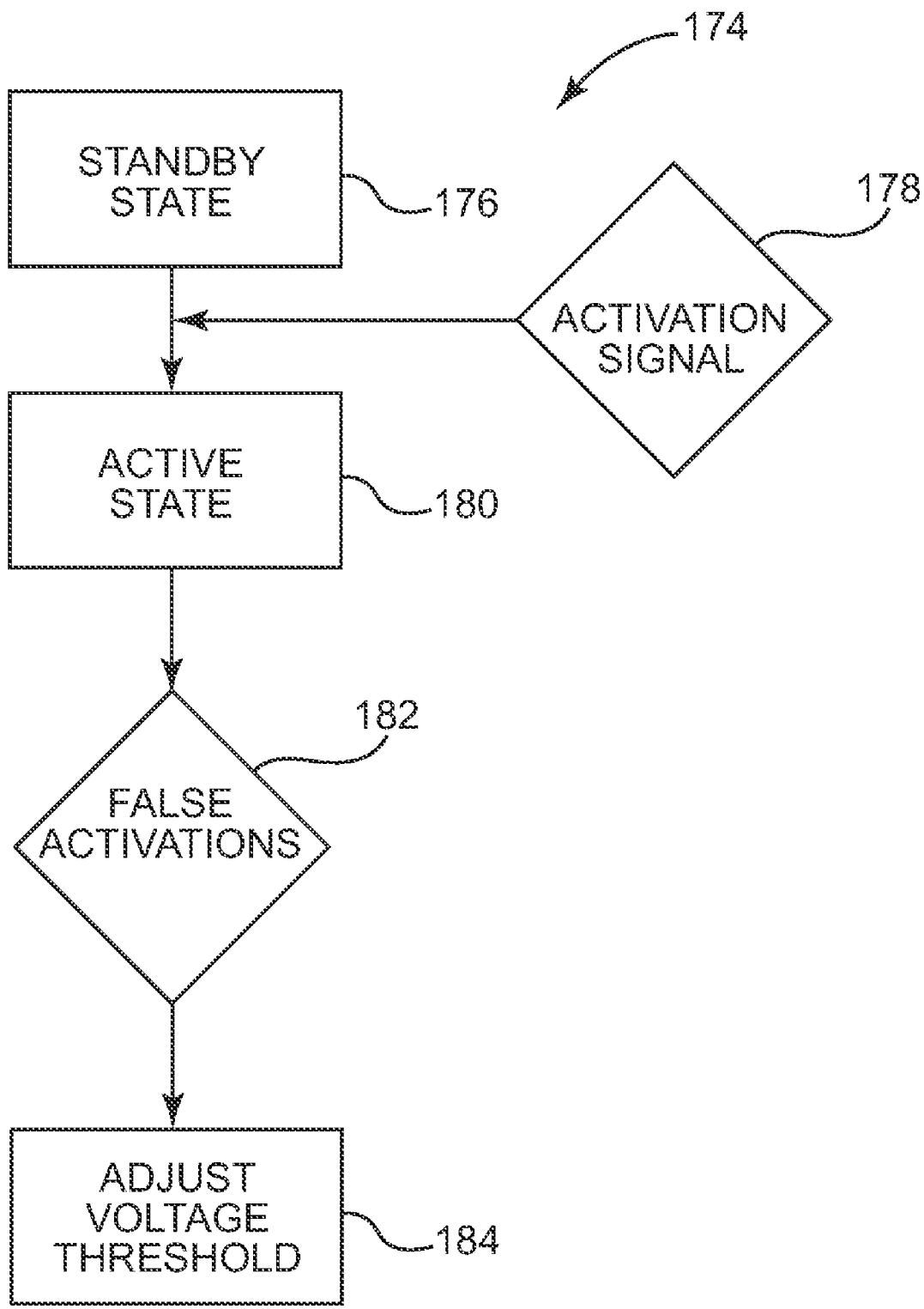
FIG. 23 is a flow diagram showing an illustrative method of dynamically adjusting the wake-up sensitivity of an implantable device.

FIG. 23 is a flow diagram showing an illustrative method 174 of dynamically adjusting the wake-up sensitivity for an implantable medical device such as the implantable device 66 of FIG. 4. First, the implantable device 66, while in its standby state (block 176), receives an activation signal, and in some embodiments a verification signal (block 178), after which the acoustic switch 80 is closed to fully activate the implantable device 66 (block 180). The implantable device 66 determines the number of false activations or otherwise estimates the probability of false activation occurrence based on sensed environmental conditions (block 182), and if it is determined that the activation sensitivity of the implantable device 66 is different from that which is necessary or desired, adjusts the AC voltage threshold of the signal detector 84 (block 184) accordingly.

In some embodiments, the control/processing circuitry 76 may adjust the AC voltage threshold in response to an on-demand external command or signal transmitted from the external device 68. One common situation where this feature may be needed is during transportation and storage of the implantable device 66 prior to implantation. In another example, during some surgical procedures, active medical devices such as implantable cardioverter defibrillators (ICDs) should be turned off. If the ICD operation is controlled by an acoustic switch, a means for desensitizing the switch may be required.

Figure 24:
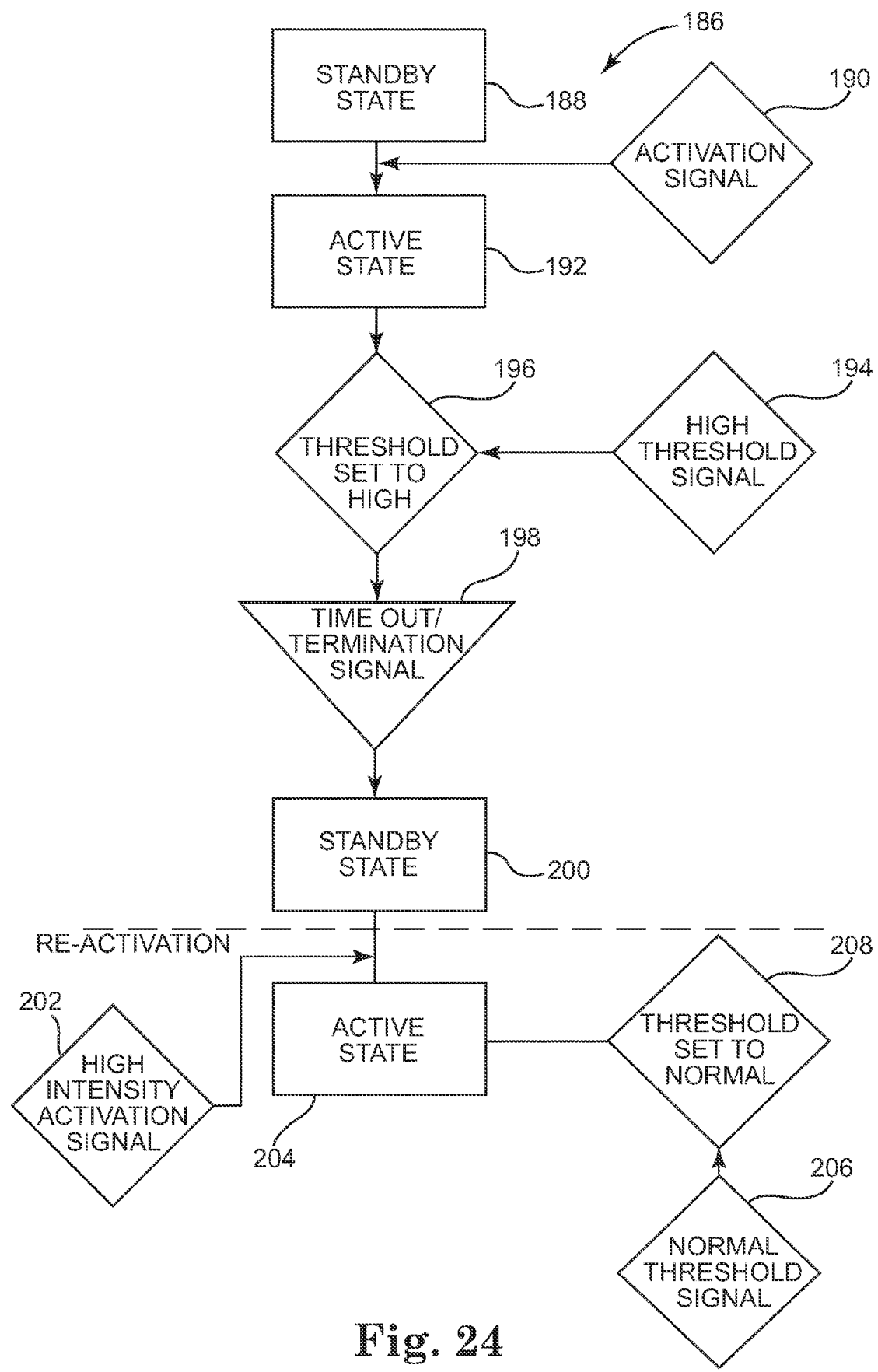
FIG. 24 is a flow diagram showing an illustrative method of dynamically adjusting the wake-up sensitivity of an implantable device.

FIG. 24 is a flow diagram showing an illustrative method of dynamically adjusting the wake-up sensitivity of an implantable device such as the implantable device 66 of FIG. 4. First, the implantable device 66, while in its standby state (block 188), receives an activation signal, and in some embodiments a verification signal (block 190), after which the acoustic switch 80 is closed to fully activate the implantable device 66 (block 192). Next, an external desensitization signal is received by the implantable device 66 (block 194), after which the AC voltage threshold of the signal detector 84 is set to a relatively high level (block 196). The relatively high AC voltage threshold will prevent false activation of the implantable device 66 during storage, shipping, or a surgical procedure, but will allow activation of the implantable device 66 using a sufficient activation signal. After receiving a deactivation signal or otherwise after a predetermined period of time (step 198), the implantable device 66 is deactivated by opening the acoustic switch 80 (block 200). After the implantable device 66 is ready for normal use, a high intensity activation signal, and in some embodiments also a verification signal, is received by the implantable device 66 (block 202), after which the implantable device 66 is activated by closing the acoustic switch 80 (block 204). Next, an externally generated signal requesting a normal AC voltage threshold is received by the implantable device 66 (block 206), after which the AC voltage threshold of the signal detector 84 is set to its normal level (block 208).

The desensitization procedure described above may also be effected by selecting from a series of different signal detectors implemented within the implantable device 66. For example, in some embodiments the implantable device 66 may include both a DC biased, high sensitivity signal detector and a lower sensitivity, unbiased signal detector. The control/processing circuitry 76 may toggle between these two signal detectors to select between the sensitized and desensitized states.

While the foregoing DC biasing and dynamic threshold methodologies lend themselves well to implantable medical devices, it should be appreciated that these methodologies could be incorporated into non-medical platforms. For example, these methodologies can be incorporated into an apparatus that does not include a medical operative element or a biocompatible casing such as inside machinery or inaccessible sensing devices such as those found behind walls or inside pipes.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A medical device, comprising:
   an energy storage device;
   at least one acoustic transducer configured to convert an acoustic signal into an alternating current (AC) electrical signal;
   at least one signal detector coupled to the at least one acoustic transducer and configured to generate an activation trigger signal when the AC electrical signal exceeds a specific trigger threshold, wherein the signal detector includes a DC biasing element that sets the specific trigger threshold, the DC biasing element configured to supply a DC biasing voltage to the signal detector;
   a control circuit; and
   a deactivation/activation switch configured to switch the medical device between an inactive state and an active state in response to the trigger signal.

2. The medical device of claim 1, wherein the at least one acoustic transducer includes a plurality of acoustic transducers.

3. The medical device of claim 1, wherein the signal detector includes a low-threshold transistor.

4. The medical device of claim 1, wherein the biasing element is a voltage biasing element, and wherein the specific threshold is a voltage threshold.

5. The medical device of claim 1, wherein the signal detector includes a Floating Gate Field-Effect Transistor (FGFET), and wherein the biasing element includes a floating gate within the FGFET.

6. The medical device of claim 5, wherein the FGFET includes a plurality of control gates electrically coupled to the floating gate, and wherein one of the control gates is configured to receive the AC electrical signal from the at least one acoustic transducer and another of the control gates is coupled to a direct current (DC) supply.

7. The medical device of claim 1, wherein the signal detector includes a Ferro-Electric Field-Effect Transistor (FEFET), and wherein the biasing element includes a ferroelectric layer within the FEFET.

8. The medical device of claim 1, wherein the signal detector includes a voltage divider circuit.

9. The medical device of claim 1, wherein the biasing element includes at least one pull-up impedance device.

10. The medical device of claim 1, wherein the biasing element includes at least one reverse-biased diode.

11. The medical device of claim 1, further including a capacitive element coupled in series with the at least one acoustic transducer.

12. The medical device of claim 11, wherein the biasing element includes a battery separate from the energy storage device, the battery coupled in parallel with the at least one acoustic transducer for charging the capacitive element.

13. The medical device of claim 11, wherein the biasing element includes one or more resistors coupled to the at least one acoustic transducer, and wherein the energy storage device is coupled to the one or more resistors to charge the capacitive element.

14. The medical device of claim 11, wherein the biasing element includes a capacitor coupled in parallel with the at least one transducer, and wherein the control circuit is operatively coupled to the capacitor to charge the capacitive element.

15. The medical device of claim 11, wherein the biasing element includes a Schottky diode coupled in parallel with the at least one acoustic transducer, the Schottky diode configured to rectify a portion of the AC electrical signal for charging the capacitive element.

16. The medical device of claim 11, wherein the biasing element includes a circuit coupled to the at least one acoustic transducer to charge the capacitive element below a threshold of instability of the circuit, and wherein the circuit is configured for being driven above the instability threshold in response to the AC electrical signal.

17. The medical device of claim 1, wherein the control circuit is configured to vary the biasing element to adjust the specific threshold.

18. The medical device of claim 1, wherein the control circuit is configured to change the state of the deactivation/activation switch if a verification signal is not received within a predetermined period of time after an activation trigger signal is generated.

19. The medical device of claim 1, wherein the at least one signal detector includes a plurality of signal detectors each having different thresholds, and wherein the control circuit is configured to dynamically adjust the specific threshold by selecting one of the signal detectors to generate an activation trigger signal.

20. The medical device of claim 1, wherein the control circuit includes a sensor for sensing environmental conditions, and wherein the control circuit is configured to adjust the specific threshold based on the sensed environmental conditions.

21. The medical device of claim 1, wherein the deactivation/activation switch is configured to switch the implantable medical device from a first state that substantially limits current flow from the energy storage device to the control circuit to a second state that allows current flow from the energy storage device to the control circuit.

22. The medical device of claim 1, wherein the medical device further includes an operative element configured for performing one or more medical functions.

23. A medical device, comprising:
an energy storage device;
at least one acoustic transducer configured to convert an acoustic signal into an alternating current (AC) electrical signal;
at least one signal detector configured to generate an activation trigger signal when the AC electrical signal exceeds a specific trigger threshold;
a control circuit configured for dynamically adjusting the specific trigger threshold;
an operative element configured for performing one or more medical functions; and
an deactivation/activation switch coupled to the energy storage device and the control circuit, wherein the deactivation/activation switch, in response to the activation trigger signal, changes from a first state that prevents current flow from the energy storage device to the control circuit to a second state that allows current flow from the energy storage device to the control circuit.

24. A system for acoustically activating a device, comprising:
a first device configured to transmit an acoustic signal; and
a second device in wireless communication with the first device, the second device including:
an energy storage device;
at least one acoustic transducer configured to convert the acoustic signal received from the first device into an alternating current (AC) electrical signal;
at least one signal detector coupled to the at least one acoustic transducer and configured to generate an activation trigger signal when the AC electrical signal exceeds a specific trigger threshold, the signal detector including a DC biasing element that sets the specific trigger threshold, the DC biasing element configured to supply a DC biasing voltage to the signal detector;
a control circuit; and
a deactivation/activation switch configured to switch the second device between an inactive state and an active state in response to the trigger signal.

* * * * *